US012576228B1

(12) United States Patent
Nye

(10) Patent No.: US 12,576,228 B1
(45) Date of Patent: Mar. 17, 2026

(54) ENDOTRACHEAL TUBE ADAPTERS

(71) Applicant: Hoyt Medical LLC, Sunfish Lake, MN (US)

(72) Inventor: Hoyt Nye, Sunfish Lake, MN (US)

(73) Assignee: Hoyt Medical LLC, Sunfish Lake, MN (US)

( * ) Notice: Subject to any disclaimer, the term of this patent is extended or adjusted under 35 U.S.C. 154(b) by 0 days.

(21) Appl. No.: 19/286,741

(22) Filed: Jul. 31, 2025

(51) Int. Cl.
| | |
|---|---|
| *A61M 16/04* | (2006.01) |
| *A61M 1/00* | (2006.01) |
| *A61M 16/08* | (2006.01) |

(52) U.S. Cl.
CPC ........ *A61M 16/0463* (2013.01); *A61M 1/741* (2021.05); *A61M 1/76* (2021.05); *A61M 16/0816* (2013.01)

(58) Field of Classification Search
CPC ..... A61B 1/00154; A61B 90/05; A61B 90/40; A61C 17/08; A61C 17/13; A61M 1/00; A61M 1/0031; A61M 1/0033; A61M 1/0043; A61M 1/0047; A61M 1/74; A61M 1/7411; A61M 1/7413; A61M 1/742; A61M 1/76; A61M 1/77; A61M 1/79; A61M 1/84; A61M 1/85; A61M 1/86; A61M 16/0409; A61M 16/0418; A61M 16/0434; A61M 16/0463; A61M 16/0465; A61M 16/0468; A61M 16/0475; A61M 16/0486; A61M 16/0488; A61M 16/0495; A61M 16/08; A61M 16/0816; A61M 16/0825; A61M 16/0833; A61M 16/0841; A61M 16/085; A61M 16/1055; A61M 16/1065; A61M 16/147; A61M 16/16; A61M 2202/0208;
(Continued)

(56) References Cited

U.S. PATENT DOCUMENTS

| | | | | |
|---|---|---|---|---|
| 3,319,628 | A | * | 5/1967 | Halligan .............. A61M 1/7411 |
| | | | | 433/91 |
| 3,767,233 | A | | 10/1973 | Hodge |

(Continued)

FOREIGN PATENT DOCUMENTS

| | | |
|---|---|---|
| GB | 2111394 A | 7/1983 |
| JP | H07323088 A | 12/1995 |

(Continued)

OTHER PUBLICATIONS

Extended European Search Report in Application No. 16821806.3, dated Jul. 9, 2018, 6 pages.
(Continued)

*Primary Examiner* — Annette Dixon
(74) *Attorney, Agent, or Firm* — Fish & Richardson P.C.

(57) ABSTRACT
An endotracheal tube adapter includes a body, an outlet at a first longitudinal end of the body, a first inlet at a second longitudinal end of the body, a second inlet on a first lateral side of the body, and a plurality of ribs on a second lateral side of the body opposite of the second inlet, the plurality of ribs extending parallel to a longitudinal axis of the body. The outlet is configured to attach to a vacuum source for drawing (i) a first portion of air or gas through the first inlet, then through an interior of the body, and then through the outlet toward the vacuum source and (ii) a second portion of air or gas through the second inlet, then through the interior, and then through the outlet toward the vacuum source.

24 Claims, 9 Drawing Sheets

(58) Field of Classification Search

CPC ...... A61M 2205/02; A61M 2205/0205; A61M 2205/0222; A61M 2205/0238; A61M 2205/33; A61M 2205/3306; A61M 2205/3327; A61M 2205/42; A61M 2205/502; A61M 2205/582; A61M 2205/583; A61M 2205/586; A61M 2205/587; A61M 2205/7536; A61M 2205/7545; A61M 2206/11; A61M 2209/06; A61M 2210/0618; A61M 2210/0625; A61M 2210/065; A61M 2210/1032; A61M 25/0074; A61M 25/01; A61M 25/0102; A61M 25/0111; A61M 3/0279; A61M 39/045; A61M 39/22; A61M 39/26; A61M 5/1418; A62B 9/04; C12M 1/00; C12M 1/32; C12M 1/36; C12M 23/48; C12M 33/04; C12M 33/12; C12M 41/00; C12Q 1/24; Y10S 128/912; Y10S 604/902; Y10T 137/7869; Y10T 137/7879; Y10T 137/86815

See application file for complete search history.

(56) References Cited

U.S. PATENT DOCUMENTS

| | | | | |
|---|---|---|---|---|
| 3,834,388 | A | * | 9/1974 | Sauer ................... A61M 39/22 604/119 |
| 3,991,762 | A | | 11/1976 | Radford |
| 4,022,218 | A | | 5/1977 | Riddick |
| 4,112,940 | A | | 9/1978 | Parkes |
| 4,193,406 | A | | 3/1980 | Jinotti |
| 4,270,778 | A | | 6/1981 | Brownell |
| 4,307,903 | A | | 12/1981 | Wallace |
| 4,351,328 | A | | 9/1982 | Bodai |
| 4,534,542 | A | | 8/1985 | Russo |
| 4,589,684 | A | | 5/1986 | Nowacki |
| 4,673,398 | A | | 6/1987 | Turner |
| 4,729,765 | A | * | 3/1988 | Eckels ................ A61M 1/7411 604/119 |
| 4,774,940 | A | | 10/1988 | Linder |
| 4,852,563 | A | | 8/1989 | Gross |
| 4,881,542 | A | | 11/1989 | Schmidt |
| 5,279,549 | A | | 1/1994 | Ranford |
| 5,509,408 | A | | 4/1996 | Kurtis |
| 5,713,348 | A | | 2/1998 | Pell |
| 5,730,727 | A | * | 3/1998 | Russo ................ A61M 1/7411 604/118 |

| | | | | |
|---|---|---|---|---|
| 6,500,164 | B1 | | 12/2002 | Turner |
| 6,958,050 | B1 | * | 10/2005 | Choski .................... A61M 1/00 604/35 |
| 7,802,574 | B2 | | 9/2010 | Schultz |
| 8,029,497 | B2 | * | 10/2011 | McCrary .............. A61M 1/7411 604/320 |
| 8,499,763 | B2 | | 8/2013 | Ledwith |
| 8,834,450 | B1 | * | 9/2014 | McCrary .............. A61M 1/7411 604/540 |
| 10,758,694 | B2 | | 9/2020 | Nye |
| 12,239,786 | B2 | | 3/2025 | Nye |
| 2002/0005197 | A1 | | 1/2002 | DeVries |
| 2003/0153897 | A1 | | 8/2003 | Russo |
| 2006/0225741 | A1 | | 10/2006 | Rothman |
| 2007/0023050 | A1 | * | 2/2007 | Janatpour ......... A61M 16/0468 128/207.15 |
| 2008/0236590 | A1 | | 10/2008 | Reissmann |
| 2011/0139151 | A1 | | 6/2011 | Burns |
| 2011/0197895 | A1 | | 8/2011 | Stephenson |
| 2011/0282326 | A1 | | 11/2011 | Krupa |
| 2012/0239435 | A1 | | 9/2012 | Ennett |
| 2012/0272955 | A1 | | 11/2012 | Cool |
| 2014/0096766 | A1 | | 4/2014 | Avitsian et al. |
| 2017/0007792 | A1 | | 1/2017 | Nye |
| 2024/0181190 | A1 | * | 6/2024 | Ferri ................. A61M 16/0488 |

FOREIGN PATENT DOCUMENTS

| | | | |
|---|---|---|---|
| JP | 2004283329 | A | 10/2004 |
| JP | 2008161672 | A | 7/2008 |
| JP | 2008295591 | A | 12/2008 |
| JP | 2013180049 | A | 9/2013 |
| JP | 2013192657 | A | 9/2013 |
| WO | WO 1994002191 | A1 | 2/1994 |
| WO | WO 1998024500 | A1 | 6/1998 |
| WO | WO 2013063520 | A1 | 5/2013 |
| WO | WO 2013116670 | A1 | 8/2013 |

OTHER PUBLICATIONS

International Preliminary Report on Patentability in International Application No. PCT/US2016/039305, mailed Jan. 18, 2018, 8 pages.

International Search Report and Written Opinion for PCT/US2016/039305, mailed Sep. 19, 2016, 21 pages.

Tibble, Adam, et al. "A Universal Airway Circuit Cap Connector (Tibblecap)". Department of Anesthesiology, University of California San Diego; 2011. (2 pages).

* cited by examiner

SECTION A-A

SECTION B-B

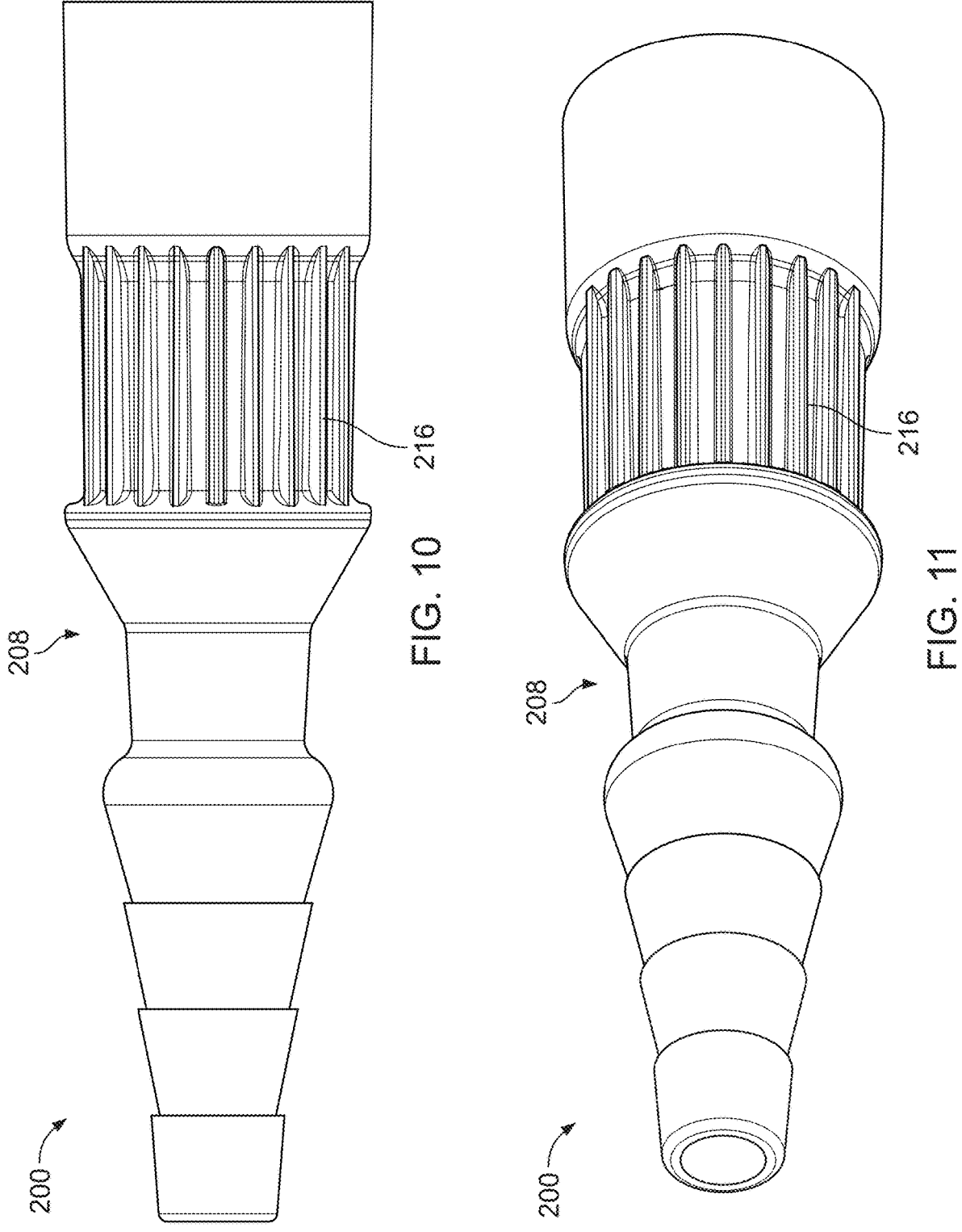

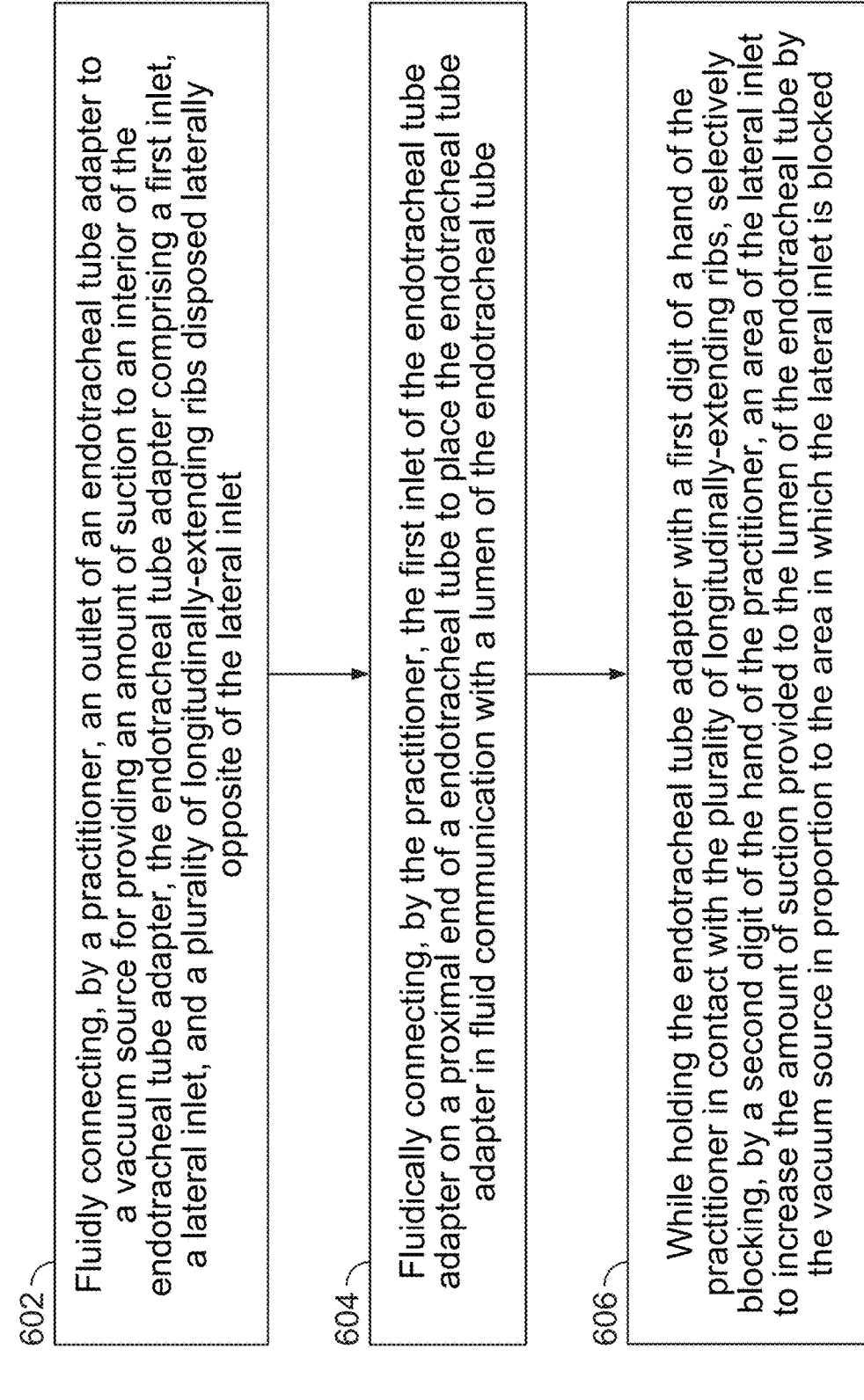

600

602 — Fluidly connecting, by a practitioner, an outlet of an endotracheal tube adapter to a vacuum source for providing an amount of suction to an interior of the endotracheal tube adapter, the endotracheal tube adapter comprising a first inlet, a lateral inlet, and a plurality of longitudinally-extending ribs disposed laterally opposite of the lateral inlet 604 — Fluidically connecting, by the practitioner, the first inlet of the endotracheal tube adapter on a proximal end of a endotracheal tube to place the endotracheal tube adapter in fluid communication with a lumen of the endotracheal tube 606 — While holding the endotracheal tube adapter with a first digit of a hand of the practitioner in contact with the plurality of longitudinally-extending ribs, selectively blocking, by a second digit of the hand of the practitioner, an area of the lateral inlet to increase the amount of suction provided to the lumen of the endotracheal tube by the vacuum source in proportion to the area in which the lateral inlet is blocked

FIG. 12

ENDOTRACHEAL TUBE ADAPTERS

TECHNICAL FIELD

This document relates to endotracheal tube adapters and methods for extracting bodily fluids from a patient's posterior pharynx while reducing the risk of trauma to patient.

BACKGROUND

Certain medical procedures, for example, an anesthetic procedure, require establishing and maintaining a patient's airway. During such procedures, a patient may be intubated with an endotracheal tube. In some cases, a patient undergoes an endotracheal intubation procedure in which an endotracheal tube is placed into and advanced through the patient's mouth, into the posterior pharynx, through the vocal cords, and into the trachea. Removing bodily fluids from the pharynx and posterior pharynx prior to and/or during the removal of the endotracheal tube is important to reduce the likelihood of excessive bodily fluids being subsequently inhaled by the patient. In some cases, inhalation of excessive bodily fluids can cause aspiration, aspiration pneumonia, and laryngospasms.

SUMMARY

The endotracheal tube adapters disclosed herein include a lateral inlet for controlling an airflow through endotracheal tube. A practitioner (e.g., a clinician such as an anesthesiologist or a nurse anesthetist) can hold the endotracheal tube adapter in one hand between two digits of that hand (e.g., between a thumb and an index finger) and use one of those digits to cover, uncover, or partially cover the lateral inlet to effectively control whether all, none, or a portion, respectively, of an airflow provided by a vacuum source should be directed through the endotracheal tube. This airflow, which is experienced as suction within the patient's airway, can be used to withdraw bodily fluids (e.g., secretions, blood, etc.) from the patient. Through a combination of maneuvering the endotracheal tube within the patient's airway and controlling how much of the lateral inlet is covered, the practitioner can effectively suction all or substantially all bodily fluids from the patient's airway.

Additional details of treating airways using adapter devices are described in U.S. Pat. Nos. 10,758,694 and 12,239,786, which are incorporated herein by reference in their entirety.

In a first aspect, an endotracheal tube adapter includes a body defining a sidewall that extends along a longitudinal axis from a first longitudinal end of the endotracheal tube adapter to a second longitudinal end of the endotracheal tube adapter. The endotracheal tube adapter includes an outlet at the first longitudinal end of the body. The endotracheal tube adapter includes a first inlet at the second longitudinal end of the body, the first inlet configured to attach to a proximal end of an endotracheal tube to fluidically connect a lumen of the endotracheal tube to an interior of the body defined by the sidewall of the body. The endotracheal tube adapter includes a second inlet along the sidewall, the second inlet on a first lateral side of the body between the first longitudinal end of the body and the second longitudinal end of the body. The endotracheal tube adapter includes a plurality of ribs on a second lateral side of the body opposite of the second inlet, the plurality of ribs extending parallel to the longitudinal axis. The outlet is configured to attach to a vacuum source for drawing (i) a first portion of air or gas through the first inlet, then through the interior of the body, and then through the outlet toward the vacuum source and (ii) a second portion of air or gas through the second inlet, then through the interior of the body, and then through the outlet toward the vacuum source.

Implementations of the endotracheal tube adapter can include one or more of the following features in any combination.

In some endotracheal tube adapters, the (i) the outlet is located on a first longitudinal half of the body, and (ii) the first inlet, the second inlet, and the plurality of ribs are located on a second longitudinal half of the body.

In some endotracheal tube adapters, a longitudinal length of the body between the first longitudinal end to the second longitudinal end is between 30 mm and 140 mm (e.g., between 70 mm and 80 mm), and a maximum diameter of the body is between 15 mm and 34 mm (e.g., between 15 mm and 20 mm).

In some endotracheal tube adapters, the second inlet has an area that can be blocked to increase an amount of suction provided to the lumen of the endotracheal tube by the vacuum source in proportion to the area in which the second inlet is blocked.

In some endotracheal tube adapters, when the vacuum source is attached to the outlet, the endotracheal tube is attached to the first inlet, the vacuum source generates suction, and the area in which the second inlet is blocked is substantially equal to an entire area of the second inlet, the first inlet and the lumen of the endotracheal tube is subjected to substantially all suction provided by the vacuum source.

In some endotracheal tube adapters, when the vacuum source is attached to the outlet, the endotracheal tube is attached to the first inlet, the vacuum source generates suction, and the second inlet is open, the lumen of the endotracheal tube is subjected to substantially no suction provided by the vacuum source.

In some endotracheal tube adapters, the plurality of ribs defines a gripping surface for a first digit of a hand of a practitioner while a second digit of the hand of the practitioner can be used to block the second inlet to increase the amount of suction provided to the endotracheal tube.

In some endotracheal tube adapters, (i) the second inlet includes a circular or an elliptical hole that extends through the sidewall of the body on the first lateral side of the body without extending through the sidewall of the body on the second lateral side of the body, and (ii) a longitudinal length of the plurality of ribs is greater than a diameter or a dimension of the second inlet.

In some endotracheal tube adapters, the second inlet includes the elliptical hole, the elliptical hole has a major axis aligned in a direction of the longitudinal axis and a minor axis aligned in a circumferential direction defined by the longitudinal axis, and the longitudinal length of the plurality of ribs is greater than (i) a first dimension of the elliptical hole along the major axis and (ii) a second dimension of the elliptical hole along the minor axis.

In some endotracheal tube adapters, the longitudinal axis defines a circumferential direction, and the plurality of ribs includes three or more ribs defining a uniform spacing the circumferential direction between each pair of adjacent ribs of the three or more ribs.

In some endotracheal tube adapters, a first side of each respective rib of the three or more ribs extends in a same direction, the same direction being transverse to the longitudinal axis.

In some endotracheal tube adapters, (i) the three or more ribs include a first rib positioned along a first radial axis extending from the longitudinal axis and a second rib positioned along a second radial axis extending from the longitudinal axis, and (ii) each rib of the three or more ribs is positioned between the first radial axis and the second radial axis.

In some endotracheal tube adapters, the three or more ribs include nine ribs disposed within a 140 degree angle (e.g., 137 degree angle) along the circumferential direction on the body.

In some endotracheal tube adapters, the body is asymmetric about a first plane that is perpendicular to the longitudinal axis and intersects each rib of the plurality of ribs and the second inlet, the body is symmetric about a second plane that extends longitudinally along the body, passes through the longitudinal axis and the second inlet, and is perpendicular to the first plane, the body is asymmetric about a third plane that is perpendicular to the first and second planes, and the third plane intersects the body without intersecting the plurality of ribs or the second inlet.

In some endotracheal tube adapters, the body is an integrally formed body including first, second, third, and fourth longitudinal sections, the first longitudinal section (i) extends from the first longitudinal end of the body to the second longitudinal section, and (ii) defines a barbed connection at the outlet of the body, the second longitudinal section extends from the first longitudinal section to the third longitudinal section, the third longitudinal section (i) extends from the second longitudinal section to the fourth longitudinal section, and (ii) defines the second inlet and the plurality of ribs, the fourth longitudinal section (i) extends from the third longitudinal section to the second longitudinal end of the body, and (ii) defines the first inlet, and the second longitudinal section has a minimum transverse dimension that less than (i) a maximum transverse dimension of the first longitudinal section, (ii) a maximum transverse dimension of the third longitudinal section, and (iii) a maximum transverse dimension of the fourth longitudinal section.

In some endotracheal tube adapters, a first longitudinal length of the first longitudinal section is greater than (i) a second longitudinal length of the second longitudinal section, (ii) a third longitudinal length of the third longitudinal section, and (iii) a fourth longitudinal length of the fourth longitudinal section.

In some endotracheal tube adapters, the second longitudinal section includes a first tapered portion having the minimum transverse dimension and extending along a first angle with respect to the longitudinal axis; and a second tapered portion that tapers radially outward from the first portion to the third longitudinal section along a second angle with respect to the longitudinal axis, the second angle being greater than the first angle.

In some endotracheal tube adapters, a first longitudinal length of the first tapered portion is substantially equal to a second longitudinal length of the second tapered portion.

In some endotracheal tube adapters, the plurality of ribs are recessed relative to a longitudinal end of the second longitudinal section in which the third longitudinal section is adjacent to, and a longitudinal end of the fourth longitudinal section in which the third longitudinal section is adjacent to.

In some endotracheal tube adapters, a first inner surface of the first longitudinal section is tapered relative to the longitudinal axis such that an inner diameter of the first longitudinal section increases from a minimum at the first longitudinal end of the body to a maximum at a longitudinal end of the first longitudinal section.

In some endotracheal tube adapters, a second inner surface of the second longitudinal section extends longitudinally from the first inner surface of the first longitudinal section and is tapered relative to the longitudinal axis such that an inner diameter of the second longitudinal section increases from a minimum at the longitudinal end of the first longitudinal section to a maximum at a longitudinal end of the second longitudinal section.

In some endotracheal tube adapters, a third inner surface of the third longitudinal section extends longitudinally from the second inner surface of the second longitudinal section and is angled relative to the longitudinal axis such that an inner diameter of the third longitudinal section increases from a minimum at the longitudinal end of the second longitudinal end to a maximum at a longitudinal end of the third longitudinal section.

In some endotracheal tube adapters, a fourth inner surface of the fourth longitudinal section extends longitudinally from the third inner surface of the third longitudinal section and is angled relative to the longitudinal axis such that an inner diameter of the fourth longitudinal section increases from a minimum at the longitudinal end of the third longitudinal section to a maximum at the second longitudinal end of the body.

In a second aspect, a method includes fluidically connecting, by a practitioner, an outlet of an endotracheal tube adapter to a vacuum source for providing an amount of suction to an interior of the endotracheal tube adapter, the endotracheal tube adapter including a first inlet, a lateral inlet, and a plurality of longitudinally-extending ribs disposed laterally opposite of the lateral inlet. The method includes fluidically connecting, by the practitioner, the first inlet of the endotracheal tube adapter on a proximal end of an endotracheal tube to place the endotracheal tube adapter in fluid communication with a lumen of the endotracheal tube. The method includes while holding the endotracheal tube adapter with a first digit of a hand of the practitioner in contact with the plurality of longitudinally-extending ribs, selectively blocking, by a second digit of the hand of the practitioner, an area of the lateral inlet to increase the amount of suction provided to the lumen of the endotracheal tube by the vacuum source in proportion to the area in which the lateral inlet is blocked.

Implementations of the second aspect can include one or more of the following features and/or the features noted above with respect to the first aspect in any combination.

Some methods include removing the endotracheal tube from a patient while selectively blocking the area of the lateral inlet of the endotracheal tube adapter.

Some methods include decreasing the area in which the lateral inlet of the endotracheal tube adapter is blocked to decrease the amount of suction provided to the lumen of the endotracheal tube by the vacuum source.

Some methods include removing the endotracheal tube from a patient while covering the lateral inlet once a distal end of the endotracheal tube has left the glottic opening of the patient.

Some methods include inserting the endotracheal tube in a mouth of a patient to position a distal end of the endotracheal tube within a trachea or a posterior pharyngeal space of the patient; and extracting bodily fluids from the patient through the lumen of the endotracheal tube while removing the endotracheal tube from the patient.

Some methods include selectively blocking the area of the lateral inlet includes rotating the endotracheal tube adapter about a longitudinal axis of the endotracheal tube adapter relative to the distal end of the endotracheal tube while (i) the endotracheal tube adapter remains rotationally fixed to the proximal end of the endotracheal tube and (ii) the endotracheal tube is being removed from the patient.

Some methods include depositing the bodily fluids in a container located fluidically between the endotracheal tube adapter and the vacuum source, the bodily fluids including secretions from the patient.

Some methods include selectively blocking the area of the lateral inlet includes rotating the endotracheal tube adapter about a longitudinal axis of the endotracheal tube adapter relative to a distal end of the endotracheal tube (e.g., by an angle of less than 90 degrees (e.g., by an angle of less than 45 degrees)) while the endotracheal tube adapter remains rotationally fixed to the proximal end of the endotracheal tube.

Some methods include rotating the endotracheal tube adapter about the longitudinal axis of the endotracheal tube adapter relative to the distal end of the endotracheal tube includes changing the endotracheal tube adapter between (i) a first configuration in which the area in which the lateral inlet is blocked is substantially equal to an entire area of the lateral inlet and the lumen of the endotracheal tube is subjected to substantially all suction provided by the vacuum source, and (ii) a second configuration in which the lateral inlet is open and the lumen of the endotracheal tube is subjected to substantially no suction provided by the vacuum source.

In some methods, the endotracheal tube adapter includes a first longitudinal section defining a barbed connection in which the vacuum source is fluidically connected, a second longitudinal section extending directly distal to the first longitudinal section, a third longitudinal section extending directly distal to the second longitudinal section, the third longitudinal section defining the lateral inlet and the plurality of longitudinally-extending ribs; and a fourth longitudinal section extending directly distal to the third longitudinal section, the fourth longitudinal section being directly attached to the proximal end of the endotracheal tube. The second longitudinal section has a minimum transverse dimension that less than (i) a maximum transverse dimension of the first longitudinal section, (ii) a maximum transverse dimension of the third longitudinal section, and (iii) a maximum transverse dimension of the fourth longitudinal section.

In some methods, the endotracheal tube adapter has a first longitudinal length of the first longitudinal section is greater than (i) a second longitudinal length of the second longitudinal section, (ii) a third longitudinal length of the third longitudinal section, and (iii) a fourth longitudinal length of the fourth longitudinal section.

In some methods, the second longitudinal section includes a first angled section and a second angled section, the first angled section extends along a first angle with respect to a longitudinal axis of the endotracheal tube adapter, the second angled section extends along a second angle with respect to the longitudinal axis of the of the endotracheal tube adapter, the second angle is greater than the first angle, and the second angled section extends directly distal to the first angled section.

In some methods, the plurality of longitudinally-extending ribs are recessed in the third longitudinal section with (i) a distal end of the second longitudinal section protruding radially beyond the plurality of longitudinally-extending ribs and (ii) a proximal end of the fourth longitudinal section protruding radially beyond the plurality of longitudinally-extending ribs.

In a third aspect, a method includes attaching, by a practitioner, a vacuum source to a proximal outlet of an endotracheal tube adapter. While a distal end of an endotracheal tube is positioned within a trachea or a posterior pharyngeal space of a patient, attaching, by the practitioner, a proximal end of the endotracheal tube to a distal inlet of the endotracheal tube adapter. While a lateral inlet of the endotracheal tube adapter is uncovered, drawing, by the vacuum source, a first airflow through the lateral inlet and then through the proximal outlet towards the vacuum source such that substantially no air flows through the endotracheal tube. While drawing the first airflow through the lateral inlet with the lateral inlet of the endotracheal tube adapter uncovered, partially withdrawing, by a hand of the practitioner, the endotracheal tube from the trachea or the posterior pharyngeal space of the patient to position the distal end of the endotracheal tube within a posterior pharynx of the patient. And while the distal end of the endotracheal tube is positioned within the posterior pharynx of the patient and while a first digit of the hand of the practitioner is in contact with a first gripping surface of the endotracheal tube adapter, at least partially covering, by a second digit of the hand of the practitioner, the lateral inlet to increase a second airflow through the endotracheal tube to suction bodily fluids from the posterior pharynx of the patient.

Implementations of the third aspect can include one or more of the following features and/or the features noted above with respect to the first and second aspects in any combination.

In some methods, the first gripping surface includes a plurality of ribs extending along a longitudinal axis of the endotracheal tube adapter.

In some methods, partially withdrawing the endotracheal tube from the trachea or the posterior pharyngeal space of the patient includes holding the endotracheal tube adapter in the hand of the practitioner and moving the endotracheal tube adapter away from the patient.

In some methods, holding the endotracheal tube adapter in the hand of the practitioner includes holding the endotracheal tube adapter in the hand of the practitioner with one or more digits of the hand of the practitioner contacting a second gripping surface of the endotracheal tube adapter, the second gripping surface being proximal or distal to the lateral inlet and the first gripping surface.

In some methods, the second gripping surface includes a necked down portion including at least one surface tapered toward a longitudinal axis of the endotracheal tube adapter for allowing the practitioner to apply a force to the at least one surface for partially withdrawing the endotracheal tube from the trachea or the posterior pharyngeal space of the patient.

In some methods, the second airflow from the posterior pharynx of the patient through the distal inlet and then through the proximal outlet towards the vacuum source is increased in proportion to an area of the lateral inlet that is covered by the second digit of the hand of the practitioner.

In some methods, when the lateral inlet is completely covered, (i) substantially no air flows through the lateral inlet of the endotracheal tube adapter and (ii) substantially all airflow provided by the vacuum source flows through the distal inlet of the endotracheal tube adapter.

In a fourth aspect, a system includes an endotracheal tube and an endotracheal tube adapter configured to be disposed on a proximal end of the endotracheal tube for fluidly connecting an interior of the endotracheal tube adapter to a lumen of the endotracheal tube. The endotracheal tube adapter includes an outlet fluidically connected to a vacuum source for providing suction to endotracheal tube, a lateral inlet having an area configured to be selectively and removably blocked to increase an amount of suction provided to the endotracheal tube by the vacuum source in proportion to the area in which the lateral inlet is blocked, and a plurality of longitudinally-extending ribs disposed opposite to the lateral inlet.

Implementations of the fourth aspect can include one or more of the following features and/or the features noted above with respect to the first through third aspects in any combination.

In some systems, the plurality of longitudinally-extending ribs define a gripping surface for a first digit of a hand of a practitioner while a second digit of the hand of the practitioner can be used to selectively and removably block the lateral inlet to increase the amount of suction provided to the endotracheal tube.

In some systems, when the outlet is fluidically connected to the vacuum source, the vacuum source provides suction, and the area in which the lateral inlet is blocked is substantially equal to an entire area of the lateral inlet, the lumen of the endotracheal tube is subjected to substantially all suction provided by the vacuum source.

In some systems, when the outlet is fluidically connected to the vacuum source, the vacuum source provides suction, and the lateral inlet is open, the lumen of the endotracheal tube is subjected to substantially no suction provided by the vacuum source.

In some systems, the endotracheal tube adapter can be rotationally fixed to the endotracheal tube and the endotracheal tube is flexible such that rotating the endotracheal tube adapter relative to a distal end of the endotracheal tube rotates a proximal end of the endotracheal tube with the endotracheal tube adapter when the endotracheal tube is fluidly connected to the endotracheal tube adapter.

In some systems, rotating the endotracheal tube adapter relative to the distal end of the endotracheal tube allows the lateral inlet to be selectively and removably blocked by a first digit of a hand of a practitioner to increase the amount of suction provided to the endotracheal tube while a second digit of the hand of the practitioner maintains contact with the plurality of longitudinally-extending ribs.

In some systems, the endotracheal tube adapter defines a substantially rigid monolithic structure.

Some systems include the vacuum source.

Some systems include a packaging, and the endotracheal tube and the endotracheal tube adapter are separated from one another within the packaging.

In some systems, the endotracheal tube adapter is disposed on the proximal end of the endotracheal tube.

In a fifth aspect, a system includes an endotracheal tube and an endotracheal tube adapter configured to be disposed on a proximal end of the endotracheal tube with an interior of the endotracheal tube adapter in fluid communication with a lumen of the endotracheal tube. The endotracheal tube adapter includes an outlet fluidically connected to a vacuum source for drawing air from the interior of the endotracheal tube adapter towards the vacuum source, a lateral inlet on a first lateral side of the endotracheal tube adapter, the endotracheal tube adapter being configured (i) allow a first airflow through the lateral inlet when the lateral inlet is uncovered while substantially limiting a second airflow through the lumen of the endotracheal tube and (ii) allow the second airflow through the lumen of the endotracheal tube when the lateral inlet is covered, and a gripping surface disposed opposite to the lateral inlet.

Implementations of the fifth aspect can include one or more of the following features and/or the features noted above with respect to the first through fourth aspects in any combination.

In some systems, the gripping surface includes a plurality of ribs extending along a longitudinal axis of the endotracheal tube adapter.

In some systems, the second airflow increases from a minimum when the lateral inlet is covered to a maximum when the lateral inlet is uncovered.

In some systems, the second airflow increases in proportion to an area in which the lateral inlet is covered.

In some systems, the endotracheal tube adapter is made of translucent polypropylene having an orange color.

Some systems include a packaging, the endotracheal tube and the endotracheal tube adapter are separated from one another within the packaging.

In some systems, the endotracheal tube adapter is disposed on the proximal end of the endotracheal tube.

In a sixth aspect, an assembly includes an endotracheal tube and an endotracheal tube adapter disposed on a proximal end of the endotracheal tube with an interior of the endotracheal tube adapter in fluid communication to a lumen of the endotracheal tube. The endotracheal tube adapter includes an outlet fluidically connected to a vacuum source for providing suction to endotracheal tube, a lateral inlet having an area configured to be selectively and removably blocked to increase an amount of suction provided to the endotracheal tube by the vacuum source in proportion to the area in which the lateral inlet is blocked, and a plurality of longitudinally-extending ribs disposed opposite to the lateral inlet.

Implementations of the sixth aspect can include one or more of the following features and/or the features noted above with respect to the first through fifth aspects in any combination.

Some assemblies include the vacuum source.

The endotracheal tube adapters, methods, systems, and assemblies disclosed herein can include one or more of the following advantages.

An endotracheal tube adapter with a lateral inlet can allow a practitioner to install the endotracheal tube with the lateral inlet uncovered so substantially no airflow (and thus no suction) is experienced at the distal end of the endotracheal tube and then, while removing the endotracheal tube from the patient, cover an area of the lateral inlet to cause a proportional amount of airflow (and thus suction) to be experienced at the distal end of the endotracheal tube. Controlling the airflow in this way can be helpful to provide suction in the patient's airway only when needed, e.g., to extract bodily fluids from the patient's posterior pharynx without exposing the patient's trachea to unnecessary suction to reduce the risk of trauma to the patient's airway.

An endotracheal tube adapter that can be placed on a proximal end of an endotracheal tube while a distal end of the endotracheal tube is in the patient's trachea is advantageous because it allows bodily fluids to be extracted as soon as the distal end of the endotracheal tube is withdrawn past the vocal cords. The lateral inlet allows the endotracheal tube adapter to be placed on the proximal end of the endotracheal tube while the distal end of the endotracheal tube is in the patient's trachea because no suction is experienced at the distal end of the endotracheal tube when the lateral inlet is uncovered. Thus, the practitioner can attach the endotracheal tube adapter to the endotracheal tube with the lateral inlet uncovered and turn on the vacuum source so that all suction passes through the lateral inlet and no suction is experienced in the patient's trachea. This can be helpful to reduce the chances of the patient having vocal cord or laryngeal spasms.

An endotracheal tube adapter with a lateral inlet can be advantageous for selectively and continuously varying the amount of suction using a digit of the practitioner. For example, a practitioner can hold the endotracheal tube adapter with their finger or thumb placed over the lateral inlet (e.g., partially or completely) to control the amount of suction at the distal end of the endotracheal tube.

Having the lateral inlet with a predetermined area can be advantageous for (i) diverting all of the suction provided by the vacuum source through the lateral inlet when the lateral inlet is completely uncovered and (ii) allowing a single digit of the practitioner's hand to completely cover the lateral inlet when diversion of suction is not necessary. For example, a lateral inlet with a predetermined area that is substantially equal to a cross-sectional area of the endotracheal tube can be particularly advantageous. Greater than 99% of endotracheal tubes used have a cross sectional diameter of between 3.0 mm (for neonates) to 8.0 mm adult men, and a few hospitals may use a 9.0 mm diameter tube for men. Having a lateral inlet with a predetermined diameter matching these diameters can be beneficial. For example, a cross sectional area between 7 mm$^2$ (for neonates) and 64 mm$^2$ (e.g., 7.1 mm$^2$, 50.3 mm$^2$, or 63.6 mm$^2$) can be beneficial.

The endotracheal tube adapters described herein provide a happy median for most practitioner finger sizes while allowing the proper sizing to maximize the lateral inlet suction and minimize the distal opening's suction force. Some designs could use a smaller lateral hole than the disclosed embodiments and/or use a lateral hole with a different shape (e.g., a circular shape would work). However, the inventor found that using an elliptical shape (oval) was the most comfortable. The optimal size for the lateral inlet can be determined using flow mechanics and studies on barotrauma at differing suction forces. The endotracheal tube adapters described herein provide approximately no force distally when the lateral inlet is uncovered (e.g., open).

The endotracheal tube adapters described herein have been able to suction water from a bowl. For example, placing the proximal end of the endotracheal tube adapter in a bowl of water (e.g., with the proximal end submerged below the water line) and, with the distal end of the endotracheal tube adapters fluidically connected to a vacuum source, varying an amount of area in which the lateral inlet (opening) is covered varies the suction force exerted on the water. For example, completely covering the lateral inlet allows to the entire suction force provided by the vacuum to be exerted on the water leading to the water being suctioned with a maximum force into the endotracheal tube adapter and the towards the vacuum source. Likewise, completely uncovering the lateral inlet allows the entire suction force provided by the vacuum to be redirected through the lateral inlet such that substantially no suction force is exerted on the water and therefore substantially no water is suctioned into the endotracheal tube adapter and towards the vacuum source. Endotracheal tube adapters having a lateral inlet with a major axis length (L2) between 7.5 mm and 12.5 mm and a minor axis length (L3) between 3 mm and 12 mm have been advantageous when used to suction water from a bowl as described in this paragraph.

An endotracheal tube adapter with a gripping surface (e.g., a plurality of longitudinally-extending ribs) disposed opposite of the lateral inlet can be advantageous for gripping, keying, and manipulating the endotracheal tube adapter within the hand of the practitioner. For example, a practitioner can grab the endotracheal tube adapter with their finger in contact with the ribs and their thumb over the lateral inlet.

An endotracheal tube adapter with ribs disposed opposite of the lateral inlet can be advantageous for improved gripping, keying, and manipulating of the endotracheal tube adapter within the hand of the practitioner. For example, the texture of the ribs can be perceived by the practitioner differently than a smooth surface. Perception of this texture can be helpful for identifying the correct placement of the endotracheal tube adapter within the hand of the practitioner. The ribs can be equally spaced and/or longitudinally extend along the endotracheal tube adapter to further provide improved gripping, keying, and manipulating of the endotracheal tube adapter within the hand of the practitioner. The ribs are also important to provide grip with the advent of oral and body secretions which invariably are on the practitioner's fingers during the time period surrounding extubation.

An endotracheal tube adapter with a plurality of longitudinally-extending ribs disposed opposite of the lateral inlet and covering less than 90 degrees of a circumference of the endotracheal tube adapter can be advantageous for improved manufacturability. For example, a two-part mold can be used in which the ribs are formed on a single side of the mold and the endotracheal tube adapter can be removed from the mold without compromising the structural integrity or design of the ribs.

An endotracheal tube adapter having a necked down section can be advantageous for gripping, keying, and manipulating the endotracheal tube adapter within the hand of the practitioner. For example, a practitioner can grip the endotracheal tube adapter with one or more fingers in contact with the necked down section with another finger over the lateral inlet and then use this grip to withdraw the endotracheal tube from the patient. In some examples, having a necked down section with at least one surface that tapers towards a longitudinal axis of the endotracheal tube adapter can be helpful to allow a practitioner to apply a force in a longitudinal direction of the endotracheal tube to withdraw the endotracheal tube from the patient's airway. Such a necked down portion can also provide a pleasing grip for the practitioner.

An endotracheal tube adapter that provides a fluid tight seal to the endotracheal tube and the vacuum source can be advantageous for flowing bodily fluids from the patient's airway to a canister located between the endotracheal tube adapter and the vacuum source while reducing leakage of the bodily fluids out of the fluid pathway between the distal end of the endotracheal tube and the canister. This can help to reduce contamination within the operating room in which the patient is intubated.

Having an endotracheal tube adapter that allows rapid control of suction during endotracheal tube removal can be advantageous for breaking up blood clots that may have formed during surgery. For example, a practitioner can create pulses air flow by quickly opening and closing (e.g., several times a second) the lateral inlet of the endotracheal tube adapter to assist in breaking up blood clots.

A colored endotracheal tube adapter can be advantageous for quickly distinguishing and identifying the endotracheal tube adapter from various other non-colored or other colored tubes and adapters that may be present during a surgical procedure. This can be helpful during time-critical applications where locating and attaching the endotracheal tube adapter on the proximal end of the endotracheal tube quickly is important. In some examples, an orange endotracheal tube adapter is beneficial for this purpose.

As used herein, distal is intended to refer to a position towards the patient and proximal is intended to refer to a position away from the patient.

The details of one or more embodiments of these systems and methods are set forth in the accompanying drawings and the description below. Other features, objects, and advantages of these systems and methods will be apparent from the description and drawings, and from the claims.

DESCRIPTION OF FIGURES

FIG. 10 is a plan view of the endotracheal tube adapter of FIG. 1.

FIG. 11 is a perspective view of the endotracheal tube of FIG. 1.

FIG. 12 is a method for using the endotracheal suction system of FIG. 1.

Like reference symbols in the various drawings indicate like elements.

DETAILED DESCRIPTION

Figure 1:
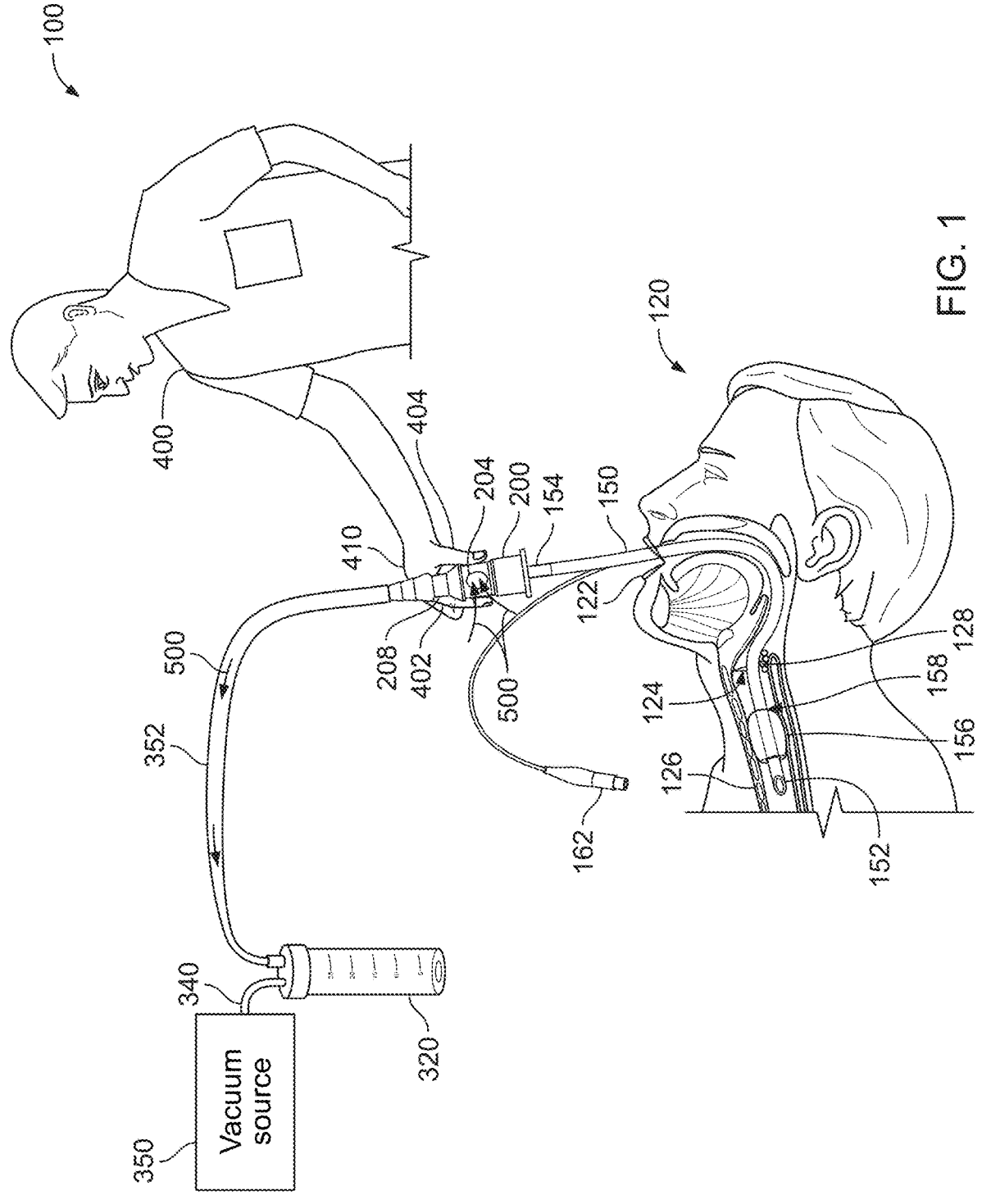
FIG. 1 shows an endotracheal suction system with an endotracheal tube adapter in a first configuration.
Figure 2:
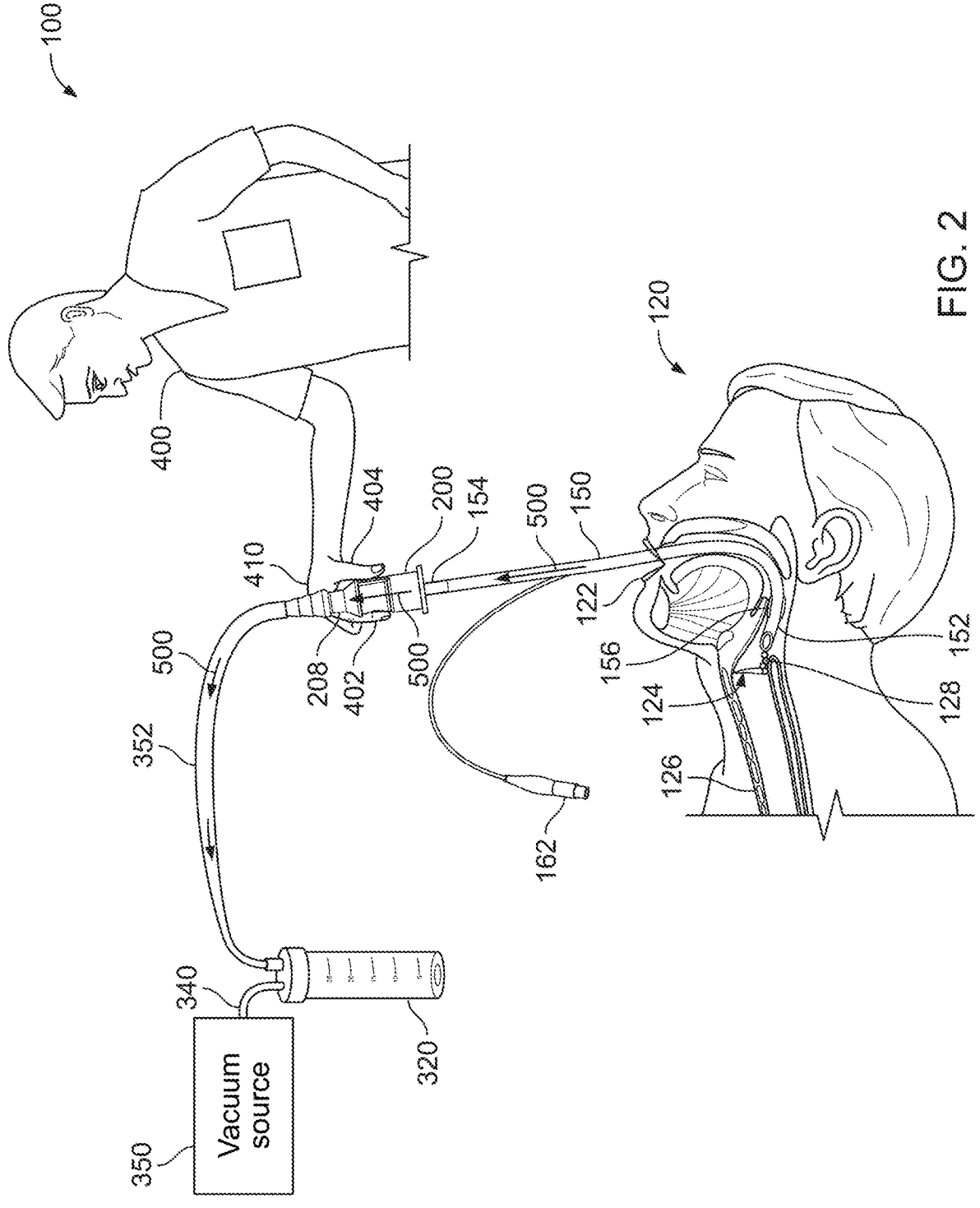
FIG. 2 shows the endotracheal suction system of FIG. 1 with the endotracheal tube adapter in a second configuration.
Figure 3:
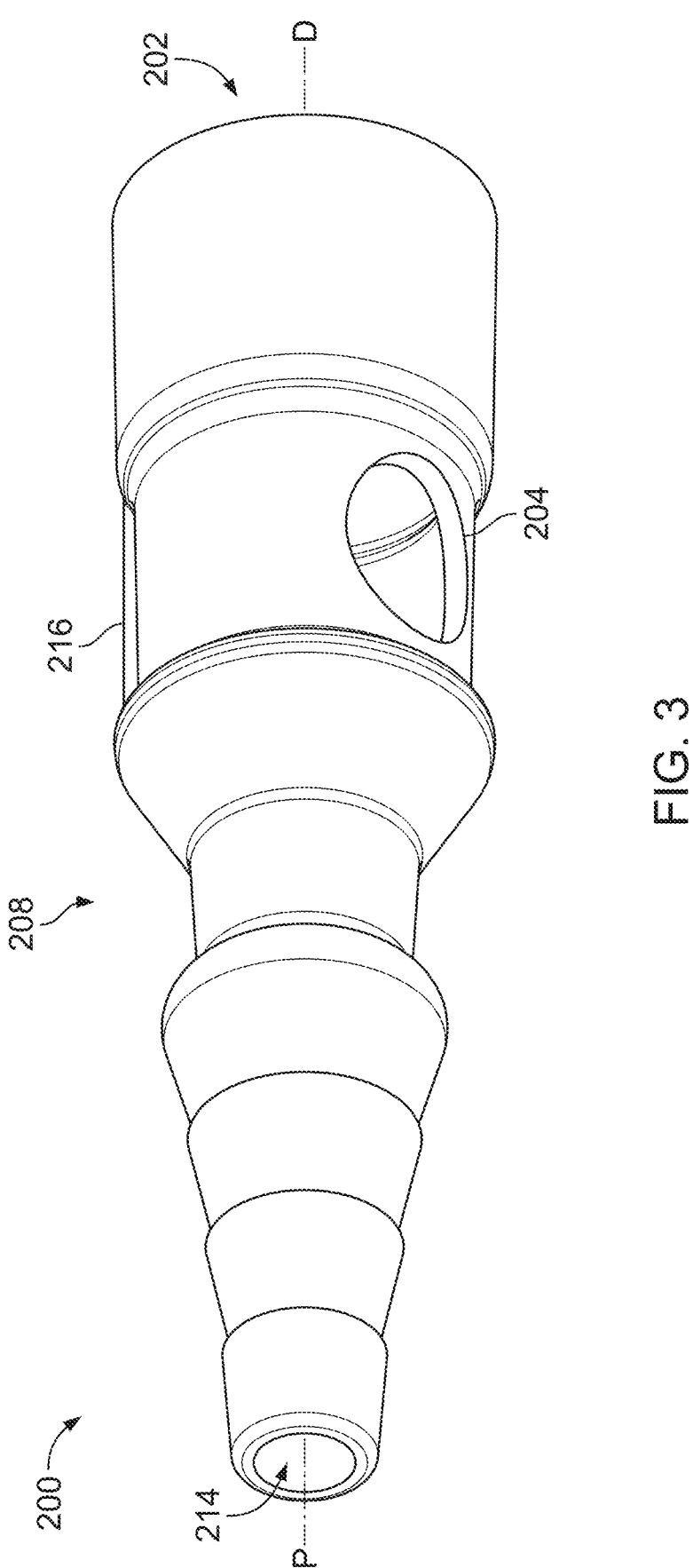
FIGS. 3 and 4 are perspective views of the endotracheal tube adapter of FIG. 1.

FIGS. 1 and 2 show a medical environment in which a patient 120 is intubated. In the example shown in FIG. 1, a practitioner 400 (e.g., an anesthesiologist or a nurse anesthetist) has inserted the endotracheal tube 150 through a mouth 122 of the patient 120 to maneuver an opening at a distal end 152 of the endotracheal tube 150 through vocal cords 124 to locate one or more openings at the distal end 152 within a trachea 126 of the patient 120. The endotracheal tube 150 has a body that defines a lumen extending from a connector at a proximal end 154 of the endotracheal tube 150 to the one or more openings at the distal end 152 of the endotracheal tube 150.

Once the distal end 152 of the endotracheal tube 150 is located within the trachea 126, the practitioner 400 can inflate a cuff 156 of the endotracheal tube 150 by pumping a pilot balloon 162 to hold the endotracheal tube 150 in a fixed position within the airway of the patient 120. The inflated cuff 156 can also substantially seal the endotracheal tube 150 to a wall within the airway of the patient 120 to limit bodily fluids 128 (e.g., secretions, blood, etc.) from moving down into the trachea 126 or the lungs of the patient 120.

The endotracheal tube 150 can be used, for example, in an anesthetic procedure or other medical procedure (e.g., surgery) in which the one or more openings at the distal end 152 within the trachea 126 deliver air or other gas (e.g., oxygen) to the patient 120. For example, a proximal end 154 of the endotracheal tube 150 can be connected to a hose attached to an anesthesia machine to deliver an anesthesia gas to the patient 120 during an anesthetic procedure, or the proximal end 154 of the endotracheal tube 150 can be connected to a hose attached to a ventilator machine to deliver oxygen to the patient 120 during surgery. Multiple gases can be delivered at the same time with the anesthesia machine and circuit.

In some patients, the endotracheal tube 150 can be a stimulus in the patient's airway causing the patient 120 to produce bodily fluids 128 such as secretions, blood, or other bodily fluids. The bodily fluids 128 need to be removed before the completion of the medical procedure. Smokers can produce more bodily fluids 128 than non-smokers. It is not uncommon for patients undergoing nasal surgery to have blood 128 accumulate within the patient's posterior pharynx. Removing this bodily fluid 128 is important for reducing the chances of the bodily fluid 128 reaching the patient's lungs which could cause aspiration or aspiration pneumonia. Aspiration is the action of either fluids or particulate matter entering the trachea, which can lead to life treating pneumonia.

While some endotracheal tubes can include a suction catheter that leads to an opening above the cuff 156 of the endotracheal tube 150, such tubes are usually exclusive for ICU patients with planned long term intubation, and are not used routinely in the operating room. However, suction catheters can be helpful for removing bodily fluids 128 from the patient 120, although it is difficult to remove all bodily fluids and ensure that all bodily fluids have been removed from the patient 120.

The practitioner 400 can administer a reversal agent (e.g., neostigmine) to the patient 120 to reverse the effects of neuromuscular paralysis. Neostigmine can be used to reverse the neuromuscular blockade agent and can cause hyper-salivation. Some newer drugs to reverse the neuromuscular blockade do not cause the hyper-salivation but cost multiple times more. Once the patient is breathing on their own to a sufficient degree, the practitioner 400 can disconnect the ventilator from the endotracheal tube 150 to stop the flow of oxygen the patient through the endotracheal tube 150.

The practitioner 400 can remove the hose at the proximal end 154 of the endotracheal tube 150 (e.g., leading to the ventilator), and connect an endotracheal tube adapter 200. This step is typically done once the patient 120 is breathing on their own since oxygen will typically no longer be supplied to the patient 120 through the endotracheal tube 150 when the endotracheal tube adapter 200 is attached.

A vacuum source 350 can be fluidly connected to the endotracheal tube adapter 200 to provide suction to remove the bodily fluids 128 from the patient 120. In some examples, the vacuum source 350 includes a vacuum pump. In some examples, the vacuum source 350 is provided as part of infrastructure of a hospital and is accessible via a wall connection within each hospital room.

Figure 4:
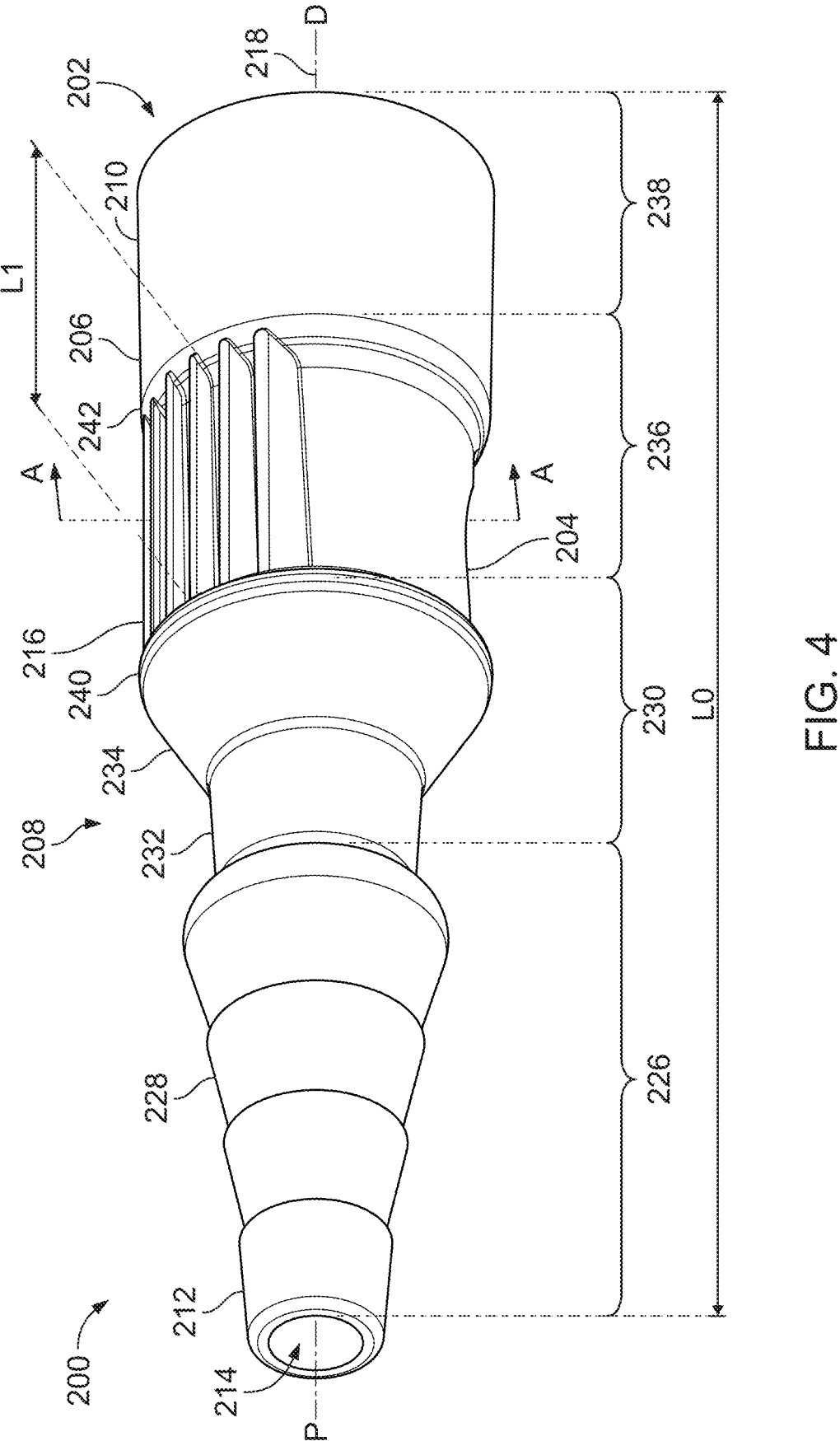
Figure 6:
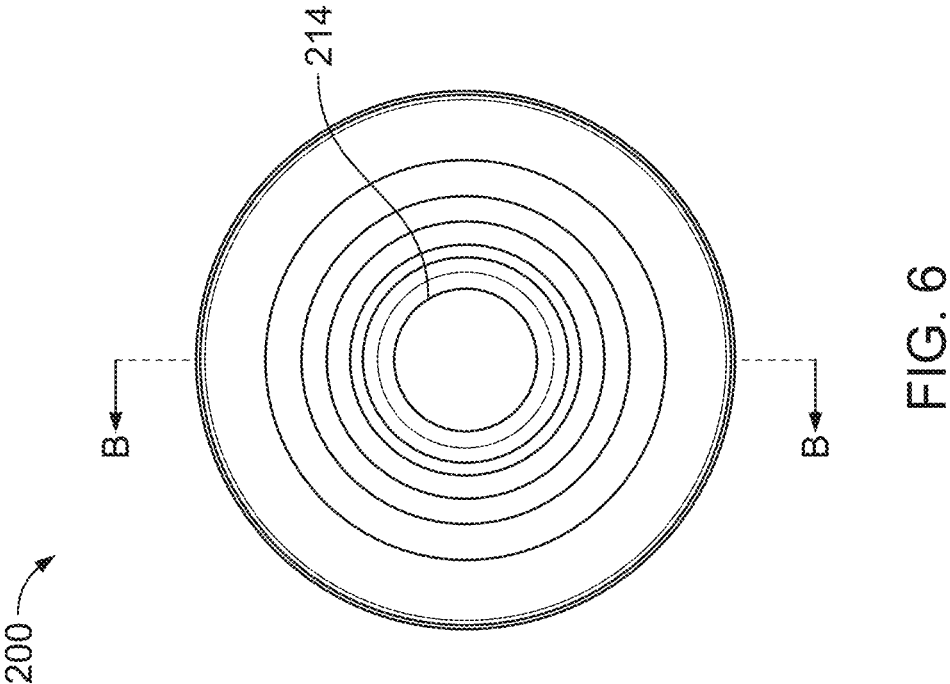
FIG. 6 is a proximal view of the endotracheal tube adapter of FIG. 1.

Referring to FIG. 4, the endotracheal tube adapter 200 includes a body 206 that extends along a longitudinal axis 218 from a first longitudinal end 212 (e.g., a distal end) to a second longitudinal end 210 (e.g., a proximal end). The endotracheal tube adapter 200 includes a first inlet 202 at the second longitudinal end 210 of the body 206 of the endotracheal tube adapter 200. The first inlet 202 is configured to attach to the proximal end 154 of the endotracheal tube 150 to fluidically connect a lumen of the endotracheal tube 150 to an interior of the body 206. The first inlet 202 is sized and dimensioned to connect to the proximal end 154 of the endotracheal tube 150. For example, the first inlet 202 can include a female connector sized and dimensioned for receiving the proximal end 154 of the endotracheal tube 150 and holding the endotracheal tube 150 in a fixed position relative to the body 206 by a frictional interference fit.

The interior of the body 206 is defined by a sidewall of the body 206. The sidewall extends from the first longitudinal end 212 of the body 206 to the second longitudinal end 210. In some examples, the first inlet 202 is fluidically connected to the lumen of the endotracheal tube 150 to allow fluid (e.g., liquid and/or gas) to flow between the lumen of the endotracheal tube 150 and the interior of the body 206 of the endotracheal tube adapter 200.

The endotracheal tube adapter 200 includes an outlet 214 that can be fluidically connected to the vacuum source 350 and a canister 320. The canister 320 is located fluidically between the endotracheal tube adapter 200 and the vacuum source 350 for collecting the bodily fluids 128. The outlet 214 is located at the first longitudinal end 212. A bore of the outlet 214 extends completely through the body 206 in a longitudinal direction. The first inlet 202 and the outlet 214 are typically circular for mating compatibility with the endotracheal tube 150 and other hoses.

The outlet 214 is configured to attach to the vacuum source 350 for drawing air or gas into the interior of the body 206. The outlet 214 is sized and dimensioned to connect to tubing connected to the vacuum source 350. For example, the outlet 214 can define a barbed connection 228 sized and dimensioned for (i) receiving a distal end of a hose 352 connected to the vacuum source 350 and (ii) holding the hose 352 in a fixed position relative to the body 206 by a frictional interference fit. The barbed connection 228 can provide a tight friction fit to the hose 352 for fluidically connecting the endotracheal tube adapter 200 to the vacuum source 350. In some examples, the outlet 214 is fluidically connected to the hose 352, which is fluidly connected to the canister 320 to allow fluid (e.g., liquid and/or gas) to flow between the interior of the body 206 of the endotracheal tube adapter 200, the hose 352, and the canister 320.

The endotracheal tube adapter 200 includes a second inlet (e.g., a lateral inlet) 204 on a first lateral side of the body 206 between the first longitudinal end 212 of the body 206 and the second longitudinal end 210 of the body 206. The second inlet 204 can be defined by a circular or elliptical opening. An area of the second inlet 204 can be covered and uncovered by the practitioner 400 to increase an airflow (and thus amount of suction) provided to the lumen of the endotracheal tube 150 by the vacuum source 350 in proportion to the area in which the second inlet 204 is blocked.

Referring back to FIG. 1, when the second inlet 204 is uncovered, the suction provided by the vacuum source 350 draws in airflow 500 from an environment surrounding the endotracheal tube adapter 200 (e.g., from the hospital room) through the second inlet 204. This results in substantially no airflow through the lumen of the endotracheal tube 150 meaning that substantially no suction is present at the distal end 152 of the endotracheal tube 150. Thus, when the second inlet 204 is uncovered, substantially no suction is experienced in the patient's airway. Since nearly all endotracheal tubes 150 have a distal opening with a diameter of less than 8.0 mm, having an opening the second inlet 204 with a diameter of approximately 8.3 mm will vent nearly all of the suction force out second inlet 204.

Referring back to FIG. 2, when the second inlet 204 is covered (e.g., by a digit of a practitioner's hand 410 (e.g., by a finger 402 or a thumb 404)), the suction provided by the vacuum source 350 draws a vacuum in the endotracheal tube

150. This results in suction provided by the vacuum source 350 at the distal end 152 of the endotracheal tube 150. Thus, when the second inlet 204 is covered, suction from the vacuum source 350 is experienced in the patient's airway. In some examples, the practitioner 400 covers the second inlet 204 once a distal end of the endotracheal tube 150 has left the glottic opening of the patient 120.

In this way, the outlet 214 is configured to attach to the vacuum source 350 for drawing (i) a first portion of air or gas through the first inlet 202, then through the interior of the body 206, and then through the outlet 214 toward the vacuum source 350 and (ii) a second portion of air or gas through the second inlet 204, then through the interior of the body 206, and then through the outlet 214 toward the vacuum source 350.

There may be situations where the practitioner 400 would like finer control over the level of the airflow experienced in the patient's airway instead of a Boolean all suction or no suction situation. For this, the practitioner 400 can cover a portion of an area of the second inlet 204 to vary the airflow at the distal end 152 of the endotracheal tube 150 and thus within the patient's airway. In some examples, the airflow provided by the vacuum source 350 experienced in the patient's airway can be directly proportional to an area in which the second inlet 204 is covered by the patient's hand 410.

For example, the practitioner 400 can cover half of the area of the second inlet 204 to provide substantially half of the airflow by the vacuum source 350 at the distal end 152 of the endotracheal tube 150. In some examples, when the area in which the second inlet 204 is blocked is substantially equal to an entire area of the second inlet 204, the lumen of the endotracheal tube 150 is subjected to substantially all airflow provided by the vacuum source 350, and when the second inlet 204 is open (e.g., substantially not blocked), the lumen of the endotracheal tube 150 is subjected to substantially no airflow provided by the vacuum source 350. Varying the suction in this way allows the practitioner 400 to control how much airflow is applied at the distal end 152 of the endotracheal tube 150.

The endotracheal tube adapter 200 can be used to vary the airflow through the endotracheal tube 150 during removal of the endotracheal tube 150 from the patient 120. It can be advantageous to attach the endotracheal tube adapter 200 to the endotracheal tube 150 with the second inlet 204 open or uncovered (as shown in FIG. 1), deflate the cuff 156 (as shown in FIG. 2), and then start removing the endotracheal tube 150 from the patient 120 by a slight upward force of the endotracheal tube adapter 200 away from the patient 120 (as shown in FIG. 2) while the suction force from the vacuum source 350 is drawn through the second inlet 204—not the endotracheal tube 150.

Referring to FIGS. 4, 5, 10, and 11, the endotracheal tube adapter 200 includes a gripping surface 216 (e.g., a plurality of ribs) on a second lateral side of the body 206 directly opposite of the second inlet 204. In some examples, the first lateral side is the side on the bottom of FIG. 7 and the second lateral side is the side on the top of FIG. 7. The ribs extend parallel to a longitudinal axis 218 of the body 206.

Figure 5:
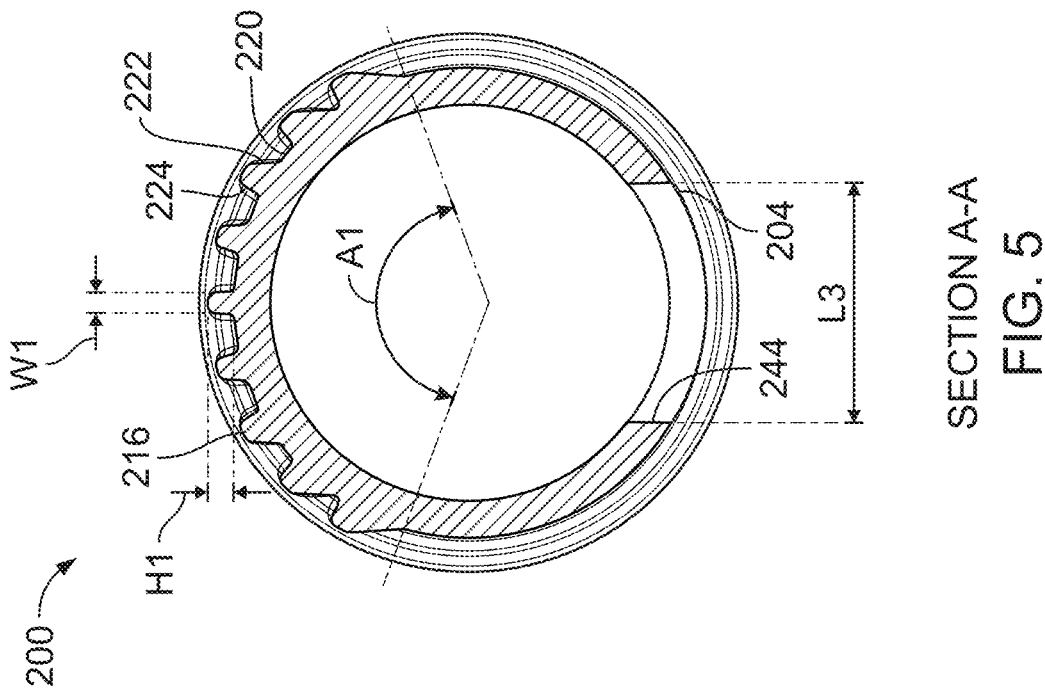
FIG. 5 is a cross-section view of the endotracheal tube adapter of FIG. 1 along section A-A.

Each rib 216 can be equally spaced from one another in a circumferential direction on the body 206. The circumferential direction is defined by the longitudinal axis 218 and extends circumferentially around the longitudinal axis 218. The ribs 216 can extend only partially around an entire circumference of the body 206 as shown in FIG. 5. All of the ribs 216 can be disposed within an angle (A1) along the circumferential direction on the body 206. In some cases, A1 is between 30 degrees and 180 degrees (e.g., 150 degrees, 140 degrees, 120 degrees, 90 degrees, 60 degrees, 45 degrees, 30 degrees, etc.). In some cases, A1 is 137 degrees.

In some examples, the plurality of ribs 216 include three or more ribs 216 defining a uniform spacing the circumferential direction between each pair of adjacent ribs 216 of the three or more ribs 216. In some examples, the three or more ribs 216 include a first rib 216 positioned along a first radial axis extending from the longitudinal axis 218 and a second rib 216 positioned along a second radial axis extending from the longitudinal axis 218. Each rib 216 of the three or more ribs 216 is positioned between the first radial axis and the second radial axis.

The endotracheal tube adapter 200 can include nine longitudinally-extending ribs 216 disposed within angle (A1) along the circumferential direction on the body 206. For example, the nine longitudinally-extending ribs 216 can be disposed within a 140 degree angle on the body 206 (e.g., a 137 degree angle).

Each rib 216 has a height (H1) protruding from an outer surface 220 of the body 206 and a width (W1). In some examples, H1 is between 0.5 mm and 1 mm (e.g., 0.87 mm). In some examples, W1 is between 0.5 mm and 1 mm (e.g., 0.72 mm). Each rib 216 can have two sides 222, 224 extending the outer surface 220 of the body 206. As shown in FIG. 5, respective first sides 222 of each rib 216 can be flat and parallel to one another and respective second sides 224 of each rib 216 can be angled to one another. In some examples, the second sides 224 extend radially from the outer surface 220 of the body 206, and the first sides 222 extend in a lateral direction from the outer surface 220.

In some examples, manufacturing at least one of the sides of the ribs 216 to be flat and parallel to one another can allow the endotracheal tube adapter 200 to be molded more economically that if all sides of the ribs were angled relative to one another. However, some endotracheal tube adapters can include ribs with first and second sides that are angled relative to one another. In some examples, having H1 between 0.5 mm and 1 mm can help with molding ease and aesthetics.

In some examples, a wall 244 of the body 206 defining the second inlet 204 extends in the same lateral direction as the first sides 222 of the ribs 216. In some examples, a first side 222 of each respective rib 216 of the three or more ribs 216 extends in the same direction. The same direction being transverse to the longitudinal axis 218. Having the wall 244 and the first sides 222 of the ribs 216 extend in the same lateral direction can further improve manufacturability of the endotracheal tube adapter 200 because it allows the endotracheal tube adapter 200 to be manufactured using a two-part mold. In some examples, the wall 244 is part of the body 206 and defines a perimeter of the second inlet 204 that extends circumferentially around the an axis of the second inlet 204. In some examples, the axis of the second inlet 204 is perpendicular to the longitudinal axis 218 of the body 206.

In some examples, the outlet 214 is located on a first longitudinal half of the body 206 (e.g., a proximal half), and the first inlet 202, the second inlet 204, and the plurality of ribs 216 are located on a second longitudinal half of the body 206 (e.g., a distal half).

Figure 7:
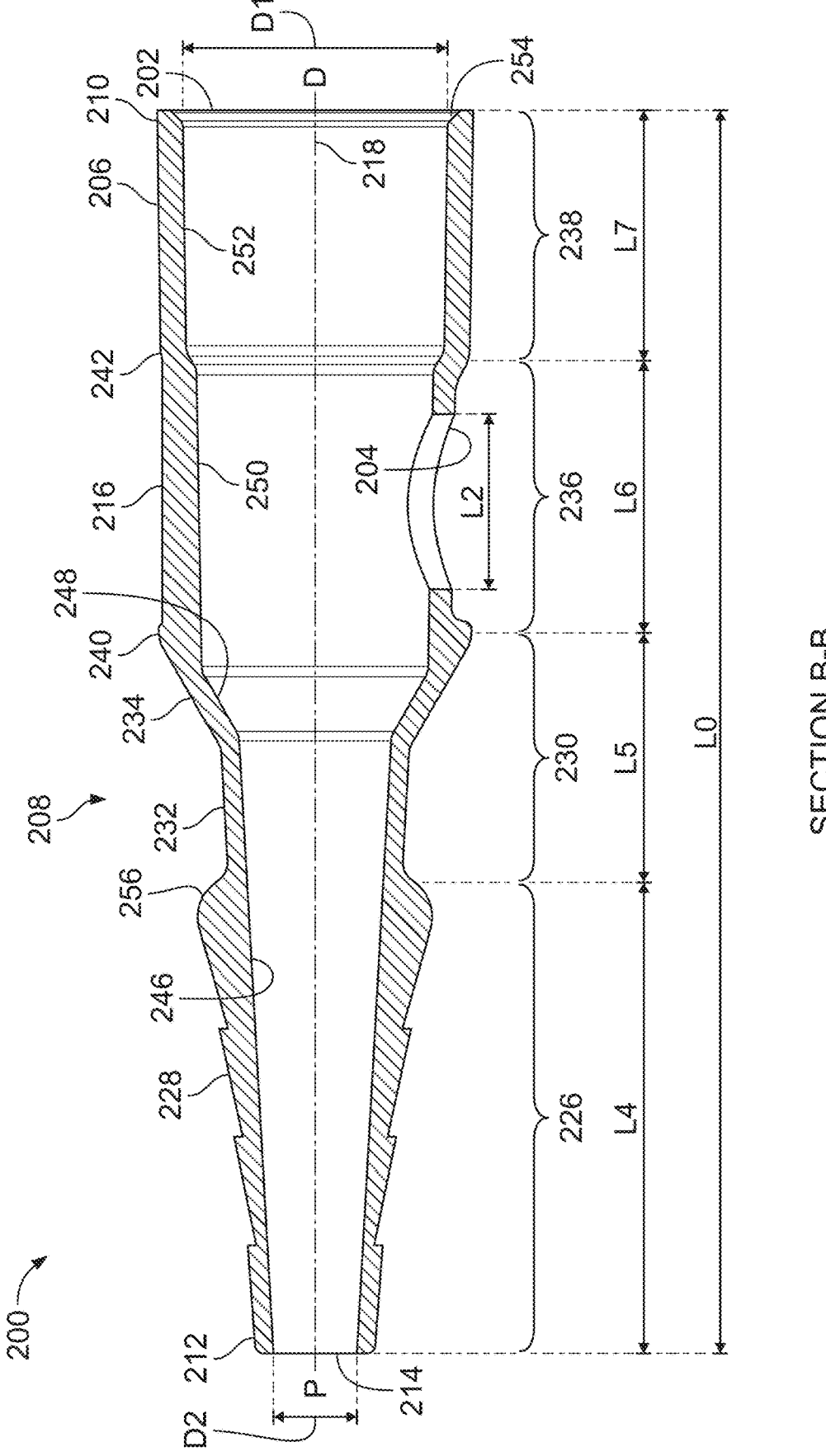
FIG. 7 is a cross-section view of the endotracheal tube adapter of FIG. 1 along section B-B.

In some examples, the body 206 is asymmetric about a first plane (e.g., the plane in which section A-A of FIG. 5 is taken) that is perpendicular to the longitudinal axis 218 and intersects each rib 216 of the plurality of ribs 216 and the second inlet 204. In some examples, the body 206 is symmetric about a second plane (e.g., the plane in which section B-B of FIG. 7 is taken) that extends longitudinally along the body 206, passes through the longitudinal axis 218 and the second inlet 204, and is perpendicular to the first plane. In some examples, the body 206 is asymmetric about a third plane that is perpendicular to the first and second planes. In some examples, the third plane intersects the body 206 without intersecting the plurality of ribs 216 or the second inlet 204.

In some examples, a longitudinal length (L0) of the body 206 between the first longitudinal end 212 and the second longitudinal end 210 is between 30 mm and 140 mm (e.g., between 70 mm and 80 mm). In some cases, L0 is 74 mm. In some examples, a maximum outer diameter of the body 206 is between 15 mm and 34 mm (e.g., between 16 mm and 25 mm). In some cases, the maximum outer diameter of the body 206 is 18.8 mm at the second longitudinal end 210 of the body 206. In some examples, a minimum outer diameter of the body 206 is between 5 mm and 10 mm. In some cases, the minimum outer diameter of the body 206 is 8.3 mm at the first longitudinal end 212 of the body 206.

Referring to FIG. 4, a longitudinal length (L1) of the ribs 216 is between 10 mm and 20 mm. In some cases, L1 is 14.5 mm. In the implementation shown, each rib 216 extends substantially parallel to the longitudinal direction without deviating in the circumferential or radial directions and each rib 216 has substantially the same length L1. However, some endotracheal tube adapters have ribs that deviate in the circumferential direction (e.g., in a spiral pattern, a chevron pattern, a cross-hatched pattern, etc.) on the outer surface 220, and/or undulate in the longitudinal direction to provide an increased gripping surface for the practitioner 400.

The size of L0 and L1 are designed for hand comfort. The side of L1 also allows for a larger lateral inlet which has several purposes. First, one needs a larger lateral inlet to have most, if not all, of the suction force to be drawn through the lateral inlet when not covered by the practitioner's finger. This reduces the possibility of potential barotrauma to the lungs. The L0 size is primarily for the increased comfort when grasping the adapter and functional utilization. The size of the adapter is designed for compatibility with endotracheal tubes so it can be provided in a package with the endotracheal tube.

Figures 8, 9:
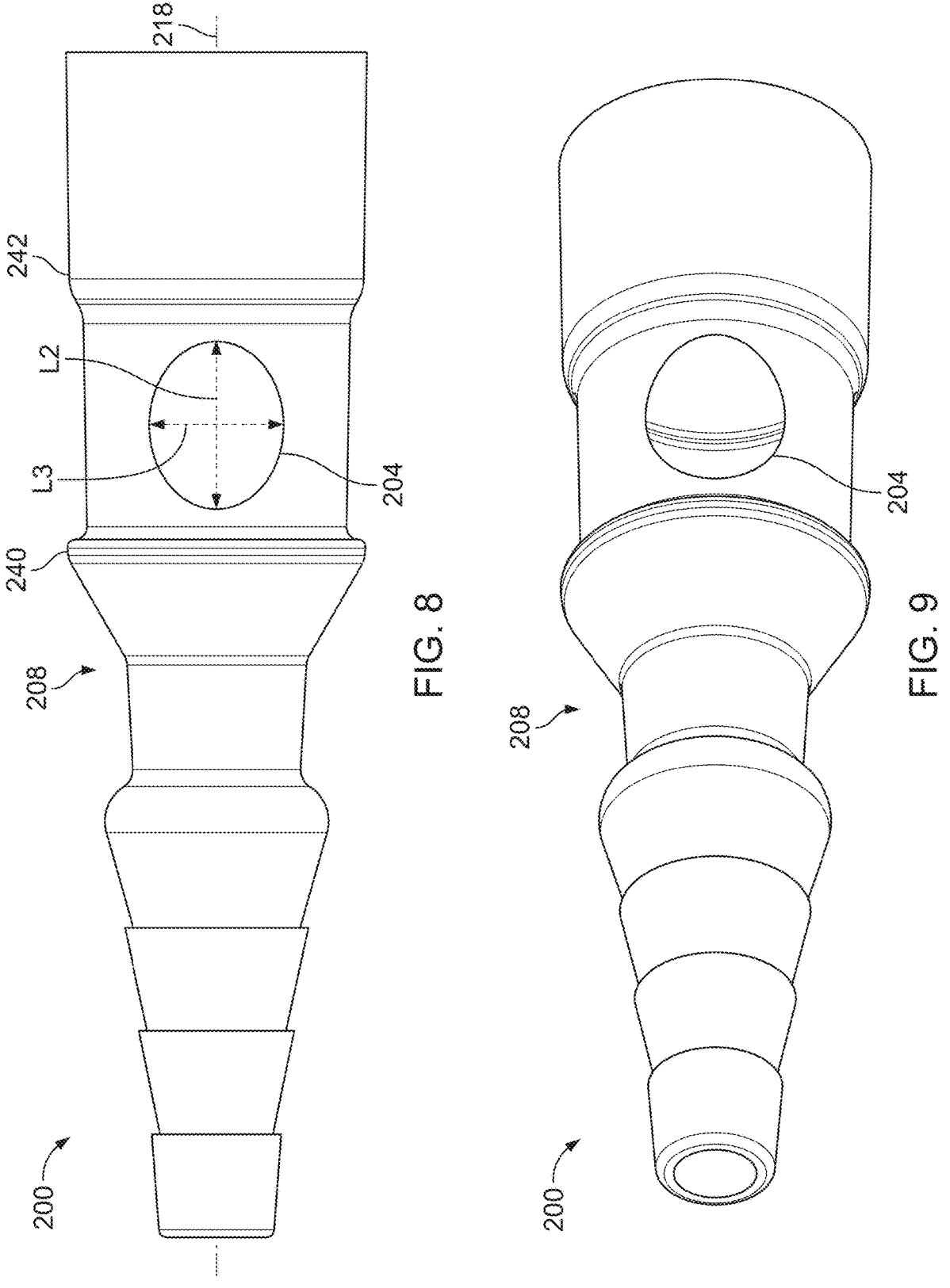
FIG. 8 is a plan view of the endotracheal tube adapter of FIG. 1.
FIG. 9 is a perspective view of the endotracheal tube adapter of FIG. 1.

Referring to FIGS. 8 and 9, the opening defining the second inlet 204 can be circular, elliptical, or any arbitrary shape (e.g., square, hexagonal, etc.). The second inlet 204 extends completely through the sidewall of the body 206 on the first lateral side of the body 206 without passing through the sidewall of the body 206 on the second lateral side of the body 206.

In the implementation shown, the opening defining the second inlet 204 is elliptical with a major axis aligned with the longitudinal axis 218 and a minor axis oriented in the circumferential direction. In some cases, a major axis length (L2) of the opening is between 7.5 mm and 12.5 mm. In some cases, L2 is 10.25 mm. In some cases, a minor axis length (L3) of the opening is between 3 mm and 12 mm. In some cases, L3 is 8.30 mm. While the opening is elliptical in the implementation shown, some endotracheal tube adapters have a circular second inlet 204 having a diameter between 3 mm and 12 mm. In some cases, the diameter can be 8.3 mm or 9.2 mm. In some cases, a circular opening is a special case in which L2=L3=the diameter.

Referring to FIGS. 4 and 7, the body 206 can be an integrally formed body that includes a first longitudinal section 226, a second longitudinal section 230, a third longitudinal section 236, and a fourth longitudinal section 238.

The first longitudinal section 226 extends from the first longitudinal end 212 of the body 206 to the second longitudinal section 230. In some examples, a first longitudinal length (L4) of the first longitudinal section 336 is between 25 mm and 35 mm. In some cases, L4 is 29 mm. The first longitudinal section 226 defines the barbed connection 228 at the outlet 214 of the body 206. The barbed connection 228 can include one or more angled surfaces. The barbed connection 228 can provide a tight friction fit to a hose 352 for fluidly connecting the endotracheal tube adapter 200 to the vacuum source 350. Each angled surface of the one or more angled surface can be angled such that a diameter at a proximal end of the respective angled surface is less than a diameter at a distal end of the respective angled surface. The body 206 can include two or three angled surfaces defining the barbed connection 228. The angles of each respective angled surface relative to the longitudinal axis 218 can increase in the distal direction. For example, an angle of a second angled surface can be larger than a first angled surface, the second angled surface being distal to the first angled surface. In some cases, each angled surface can be flat.

An outlet diameter (D1) of the outlet 214 can be less than (i) a first inlet diameter (D2) of the first inlet 202 and (ii) a second inlet dimension (e.g., L2, L3, or a diameter) of the second inlet 204. The barbed connection 228 can be integrally formed in the sidewall at the proximal end 212 of the body 206 such that the proximal end of the barbed connection 228 defines the first inlet diameter (D2) of the first inlet 202.

The second longitudinal section 230 extends from the first longitudinal section 226 to the third longitudinal section 236. In some examples, a second longitudinal length (L5) of the second longitudinal section 230 is between 10 mm and 20 mm. In some cases, L5 is 14.5 mm.

The second longitudinal section 230 can include a necked down section 208. The necked down section 208 has a minimum transverse dimension that less than (i) a maximum transverse dimension of the first longitudinal section 226, (ii) a maximum transverse dimension of the third longitudinal section 236, and (iii) a maximum transverse dimension of the fourth longitudinal section 238. The necked down section 208 can include a first tapered portion 232 and a second tapered portion 234. The first tapered portion 232 extends distally and radially outward from the minimum transverse dimension of the necked down section 208 along a first angle with respect to the longitudinal axis 218 of the body 206 to the second tapered portion 234. The second tapered portion 232 extends distally and radially outward from the first tapered portion 232 along a second angle with respect to the longitudinal axis 218 of the body 206 to a distal end of the necked down section 208. The second angle can be greater than the first angle. The second tapered portion 234 has a surface that is tapered towards the longitudinal axis 218 of the body 206.

In some examples, a first longitudinal length of the first angled section 232 is substantially equal to a second longitudinal length of the second angled section 234. For example, the first longitudinal length can be between 5 mm and 10 mm (e.g., 7.8 mm) and the second longitudinal length can be between 5 mm and 10 mm (e.g., 8.1 mm). In some cases, the first longitudinal length and the second longitudinal length sum to L5. In some examples, a minimum outer diameter of the necked down section 208 is between 7.5 mm and 12.5 mm. In some cases, the minimum outer diameter of the necked down section 208 is 10.4 mm.

In some examples, the distal end of the first longitudinal section 226 transitions into the second longitudinal section 230 by a curved surface (e.g., a knob) 256. In some cases, the curved surface 256 can be sized to provide a comfortable surface for the hand 410 of the practitioner 400 when the practitioner holds the endotracheal tube adapter 200. In some examples, a radius of the curved surface 256 is between 0.05 mm and 0.2 mm. In some examples, the radius of the curved surface 256 is 0.1 mm.

The body 206 can include a third longitudinal section 236 that extends from the second longitudinal section 230 to the fourth longitudinal section 238. The third longitudinal section 236 defines the second inlet 204 and the plurality of ribs 216. In some examples, a third longitudinal length (L6) of the third longitudinal section 236 is between 10 mm and 20 mm. In some cases, L6 is 15.4 mm.

The ribs 216 define the gripping surface for a first digit (e.g., finger 402 or thumb 404) of the hand 410 of the practitioner 400 while a second digit (e.g., the other of the finger 402 or thumb 404) of the hand 410 of the practitioner 400 can be used to selectively and removably block the second inlet 204 to increase the amount of suction provided to the endotracheal tube 150.

Referring to FIGS. 7 and 8, the ribs 216 can be recessed relative to a longitudinal end (e.g., a distal end) 240 of the second longitudinal section 230 in which the third longitudinal section 236 is adjacent to, and a longitudinal end (e.g., a proximal end) 242 of the fourth longitudinal section 238 in which the third longitudinal section 236 is adjacent to. In some examples, the ribs 216 can be recessed in the third longitudinal section 236 with (i) the distal end 240 of the second longitudinal section 230 protruding radially outward beyond ribs 216 and (ii) the proximal end 242 of the fourth longitudinal section 238 protruding radially outward beyond the ribs 216.

The body 206 can include a fourth longitudinal section 238 that extends from the third longitudinal section 236 to the second longitudinal end 210 of the body 206. The fourth longitudinal section 238 defines the first inlet 202. In some examples, a third longitudinal length (L7) of the fourth longitudinal section 238 can be between 10 mm and 20 mm. In some cases, L7 is 15.3 mm.

The body 206 can be an integrally formed monolithic body that includes the first longitudinal section 226, the second longitudinal section 230, the third longitudinal section 236, and the fourth longitudinal section 238. In some cases, the endotracheal tube adapter 200 defines a substantially rigid monolithic structure. An entirety of the body 206 can be an integrally formed body. In addition, the first longitudinal length (L4) can be greater than (i) the second longitudinal length (L5), (ii) the third longitudinal length (L6), and (iii) the fourth longitudinal length (L7).

In some examples, the body 206 is made of a plastic material. In some cases, the body 206 is made of polypropylene. In some cases, the body 206 is manufactured using a two-part mold. In some cases, the body 206 is colored (e.g., orange). In some cases, the body 206 is translucent. In some cases, the body 206 is colored so the practitioner 400 can more quickly identify the endotracheal tube adapter 200 from other plastic components on a surgical table. Saving time can be important in certain surgical procedures. In some cases, the body 206 is orange, translucent, and made of polypropylene. In some cases, the body 206 is colored based on (e.g., to match) the colors of colleges or sport teams that are local to the practitioner.

Referring to FIG. 7, a first inner surface 246 of the first longitudinal section 226 can be angled relative to the longitudinal axis 218 such that an inner diameter of the first longitudinal section 226 increases from a minimum at the proximal end of the first longitudinal section 226 to a maximum at the distal end of the first longitudinal section 226.

A second inner surface 248 of the second longitudinal section 230 extends distally from the first inner surface 246 of the first longitudinal section 226. The second inner surface 248 can be angled relative to the longitudinal axis 218 such that an inner diameter of the second longitudinal section 230 increases from a minimum at the proximal end of the second longitudinal section 230 to a maximum at the distal end of the second longitudinal section 230. In some examples, a minimum diameter of the second longitudinal section 230 is equal to a maximum diameter of the first longitudinal section 226.

A third inner surface 250 of the third longitudinal section 236 extends distally from the second inner surface 248 of the second longitudinal section 230. The third inner surface 250 can be angled relative to the longitudinal axis 218 such that an inner diameter of the third longitudinal section 236 increases from a minimum at the proximal end of the third longitudinal section 236 to a maximum at the distal end of the third longitudinal section 236. In some examples, a minimum diameter of the third longitudinal section 236 is equal to a maximum diameter of the second longitudinal section 230.

A fourth inner surface 252 of the fourth longitudinal section 238 extends distally from the third inner surface 250 of the third longitudinal section 236. The fourth inner surface 252 can be angled relative to the longitudinal axis 218 such that an inner diameter of the fourth longitudinal section 238 increases from a minimum at the proximal end of the fourth longitudinal section 238 to a maximum at the distal end of the fourth longitudinal section 238. In some examples, a minimum diameter of the fourth longitudinal section 238 is equal to a maximum diameter of the third longitudinal section 236. In some examples, the fourth inner surface 252 at the distal end of the body 206 has a taper 254. In some cases, the taper 254 has a 45 degree angle relative to the longitudinal axis 218.

In some examples, the endotracheal tube 150 and the endotracheal tube adapter 200 are part of an endotracheal suction system. In some examples, the endotracheal suction system is provided as an assembly or as a kit to the practitioner 400. For example, the system can include the endotracheal tube 150 and the endotracheal tube adapter 200 separated from one another in a packaging. Once removed from the packaging, the endotracheal tube adapter 200 can be fluidly connected to the proximal end 154 of the endotracheal tube 150 with an interior of the endotracheal tube adapter 200 in fluid communication with a lumen of the endotracheal tube 150.

As described above, the endotracheal tube adapter 200 can include the outlet 214 fluidically connected to a vacuum source 350 for providing suction to endotracheal tube 150. The endotracheal tube adapter 200 can include the inlet 204 configured to increase an amount of suction provided to the endotracheal tube 150 by the vacuum source 350 in proportion to an area in which the inlet 204 is blocked. In some examples, the inlet 204 is configured to increase the amount of suction by being sized and dimensioned such that an area of the inlet 204 can be selectively and removably blocked to increase the amount of suction provided to the endotracheal tube 150 by the vacuum source 350 in proportion to the area in which the inlet 204 is blocked.

In some cases, when the area in which the inlet 204 is blocked is substantially equal to an entire area of the inlet 204, the lumen of the endotracheal tube 150 is subjected to substantially all suction provided by the vacuum source 350. In some cases, when the inlet 204 is open (e.g., the area in which the inlet 204 is blocked is substantially equal to zero or negligible), the lumen of the endotracheal tube 150 is subjected to substantially no suction provided by the vacuum source 350.

The endotracheal tube adapter 200 can include the gripping surface (e.g., a plurality of longitudinally-extending ribs) 216 disposed opposite to the inlet 204. In some cases, the ribs 216 define a gripping surface for a first digit (e.g., one of a finger 402 or a thumb 404) of a hand 410 of a practitioner 400 while a second digit (e.g., the other of the finger 402 or the thumb 404) of the hand 410 of the practitioner 400 can be used to selectively and removably block the inlet 204 to increase the amount of suction provided to the endotracheal tube 150.

In some cases, the endotracheal tube adapter 200 is rotationally fixed to the endotracheal tube 150 and the endotracheal tube 150 is flexible such that rotating the endotracheal tube adapter 200 relative to a distal end 152 of the endotracheal tube 150 rotates a proximal end 154 of the endotracheal tube 150 with the endotracheal tube adapter 200. In some cases, the endotracheal tube 150 is made of a translucent flexible plastic material such as polypropylene.

In some cases, rotating the endotracheal tube adapter 200 relative to the distal end 152 of the endotracheal tube 150 allows the inlet 204 to be selectively and removably blocked by a first digit (e.g., one of a finger 402 or a thumb 404) of a hand 410 of a practitioner 400 to increase the amount of suction provided to the endotracheal tube 150 while a second digit (e.g., the other of the finger 402 or the thumb 404) of the hand 410 of the practitioner 400 maintains contact with the ribs 216.

FIG. 12 shows a method 600 for using the endotracheal suction system that includes the endotracheal tube adapter 200 and the endotracheal tube 150. In some examples, one or more steps (e.g., all steps) of the method 600 can be performed by the practitioner 400.

At step 602, the method 600 includes fluidically connecting, by a practitioner 400, the outlet 214 of the endotracheal tube adapter 200 to a vacuum source 350 for providing an amount of suction to an interior of the endotracheal tube adapter 200. The endotracheal tube adapter 200 includes the first inlet 202, the lateral inlet 204, and the plurality of longitudinally-extending ribs 216 disposed laterally opposite of the lateral inlet 204. In some examples, this involves physically attaching the outlet 214 of the endotracheal tube adapter 200 to a hose fluidly connected to the vacuum source 350.

At step 604, the method 600 includes fluidly connecting, by the practitioner 400, the first inlet 202 of the endotracheal tube adapter 200 on the proximal end 154 of the endotracheal tube 150 to place the endotracheal tube adapter 200 in fluid communication with the lumen of the endotracheal tube 150. In some examples, this involves physically attaching the first inlet 202 of the endotracheal tube adapter 200 to the proximal end 154 of the endotracheal tube 150. In some examples, the endotracheal tube adapter 200 is attached to the vacuum source 350 before being attached to the endotracheal tube 150. In other examples, the endotracheal tube adapter 200 is attached to the vacuum source 350 after being attached to the endotracheal tube 150.

At step 606, the method 600 includes while holding the endotracheal tube adapter 200 with a first digit (e.g., one of a finger 402 or a thumb 404) of a hand 410 of the practitioner 400 in contact with the ribs 216, selectively blocking, by a second digit (e.g., the other of the finger 402 or the thumb 404) of the hand 410 of the practitioner 400, an area of the lateral inlet 204 to increase the amount of suction provided to the lumen of the endotracheal tube 150 by the vacuum source 350 in proportion to the area in which the lateral inlet 204 is blocked.

In some examples, the method 600 includes removing the endotracheal tube 150 from the patient 120 while selectively blocking the area of the lateral inlet 204 of the endotracheal tube adapter 200.

In some examples, the method 600 includes decreasing the area in which the lateral inlet 204 of the endotracheal tube adapter 200 is blocked to decrease the amount of suction provided to the lumen of the endotracheal tube 150 by the vacuum source 350.

In some examples, the method 600 includes removing the endotracheal tube 150 from a patient 120 while decreasing the area in which the lateral inlet 204 of the endotracheal tube adapter 200 is blocked.

In some examples, the method 600 includes inserting the endotracheal tube 150 in a mouth 122 of a patient 120 to position a distal end 152 of the endotracheal tube 150 within a trachea 126 of the patient 120. Some practitioners may attach the suction hose after the endotracheal tube 150 has left the trachea 126 and entered the hypopharyngeal area. In such cases, the distal end 152 of the endotracheal tube 150 can be located within a posterior pharyngeal space of the patient 120, and the method 600 can include inserting the endotracheal tube 150 in the mouth 122 of the patient 120 to position the distal end 152 of the endotracheal tube 150 within the posterior pharyngeal space of the patient 120.

In some examples, the method 600 includes extracting bodily fluids 128 from the patient 120 through the lumen of the endotracheal tube 150 while removing the endotracheal tube 150 from the patient 120.

In some examples, selectively blocking the area of the lateral inlet 204 includes rotating the endotracheal tube adapter 200 about a longitudinal axis 218 of the endotracheal tube adapter 200 relative to the distal end 152 of the endotracheal tube 150 while (i) the endotracheal tube adapter 200 remains rotationally fixed to the proximal end 154 of the endotracheal tube 150 and (ii) the endotracheal tube 150 is being removed from the patient 120.

In some examples, the method 600 includes depositing the bodily fluids 128 in a canister 320 located fluidically between the endotracheal tube adapter 200 and the vacuum source 350.

In some examples, selectively blocking the area of the lateral inlet 204 includes rotating the endotracheal tube adapter 200 about a longitudinal axis 218 of the endotracheal tube adapter 200 relative to a distal end 152 of the endotracheal tube 150 by an angle of less than 45 degrees (e.g., 20 degrees, 30 degrees, etc.) while the endotracheal tube adapter 200 remains rotationally fixed to the proximal end 154 of the endotracheal tube 150.

In some examples, rotating the endotracheal tube adapter 200 about the longitudinal axis 218 of the endotracheal tube adapter 200 relative to the distal end 152 of the endotracheal tube 150 by the angle of less than 45 degrees includes changing the endotracheal tube adapter 200 between (i) a first configuration in which the area in which the lateral inlet 204 is blocked is substantially equal to an entire area of the lateral inlet 204 and the lumen of the endotracheal tube 150 is subjected to substantially all suction provided by the vacuum source 350, and (ii) a second configuration in which the lateral inlet 204 is open (e.g., the area in which the lateral inlet 204 is blocked is substantially zero or negligible) and the lumen of the endotracheal tube 150 is subjected to substantially no suction provided by the vacuum source 350.

In some examples, selectively blocking the area of the lateral inlet 204 includes repeatedly blocking (e.g., three or more times) the lateral inlet 204 to provide a pulsed vacuum at the distal end 152 of the endotracheal tube 150. In some examples, the pulsed vacuum can be used to break up one or more blockages within the patient's airway. In some examples, the pulsed vacuum can be used to break up blood clots within the patient's airway. For example, the practitioner 400 can create pulses air flow by quickly opening and closing (e.g., several times a second) the lateral inlet 204 of the endotracheal tube adapter 200 to assist in breaking up blood clots.

In some examples, the following method can be used in addition to, or instead of, method 600.

The practitioner 400 can attach the vacuum source 350 to the proximal outlet 214 of the endotracheal tube adapter 200. While a distal end 152 of an endotracheal tube 150 is positioned within a trachea or a posterior pharyngeal space of a patient 120, attaching, by the practitioner 400, a proximal end 154 of the endotracheal tube 150 to a distal inlet 202 of the endotracheal tube adapter 200.

While a lateral inlet 204 of the endotracheal tube adapter 200 is uncovered, drawing, by the vacuum source 350, a first airflow through the lateral inlet 204 and then through the proximal outlet 214 towards the vacuum source 350 such that substantially no air flows through the endotracheal tube 150.

While drawing the first airflow through the lateral inlet 204 with the lateral inlet 204 of the endotracheal tube adapter 200 uncovered, partially withdrawing, by the hand 410 of the practitioner 400, the endotracheal tube 150 from the trachea or the posterior pharyngeal space of the patient 120 to position the distal end 152 of the endotracheal tube 150 within a posterior pharynx of the patient 120.

While the distal end 152 of the endotracheal tube 150 is positioned within the posterior pharynx of the patient 120 and while a first digit (e.g., one of the finger 402 or the thumb 404) of the hand 410 of the practitioner is in contact with a first gripping surface 216 of the endotracheal tube adapter 200, at least partially covering, by a second digit (e.g., the other of the finger 402 or the thumb 404) of the hand 410 of the practitioner 400, the lateral inlet 204 to increase a second airflow through the endotracheal tube 150 to suction bodily fluids from the posterior pharynx of the patient 120. In some examples, the first gripping surface 216 comprises the plurality of ribs 216 extending along the longitudinal axis 218 of the endotracheal tube adapter 200.

In some examples, partially withdrawing the endotracheal tube 150 from the trachea or the posterior pharyngeal space of the patient 120 includes holding the endotracheal tube adapter 200 in the hand 410 of the practitioner 400 and moving the endotracheal tube adapter 200 away from the patient 120. In some cases, holding the endotracheal tube adapter 200 in the hand 410 of the practitioner 400 includes holding the endotracheal tube adapter 200 in the hand 410 of the practitioner 400 with one or more digits of the hand 410 of the practitioner 400 contacting a second gripping surface 208 of the endotracheal tube adapter 200. The second gripping surface being proximal to the lateral inlet 204 and the first gripping surface 216. In some examples, the second gripping surface includes a necked down section 208. In some examples, a second gripping surface is distal to the lateral inlet 204.

In some examples, the necked down section 208 includes at least one surface tapered toward a longitudinal axis 218 of the endotracheal tube adapter 200 for allowing the practitioner 400 to apply a force to the at least one surface for partially withdrawing the endotracheal tube 150 from the trachea or posterior pharyngeal space of the patient 120.

In some examples, the second airflow from the posterior pharynx of the patient 120 through the distal inlet 202 and then through the proximal outlet 214 towards the vacuum source 350 is increased in proportion to an area of the lateral inlet 204 that is covered by the second digit of the hand 410 of the practitioner 400. In some examples, when the lateral inlet 204 is completely covered, (i) substantially no air flows through the lateral inlet 204 of the endotracheal tube adapter 200 and (ii) substantially all airflow provided by the vacuum source 350 flows through the distal inlet 202 of the endotracheal tube adapter 200.

While the endotracheal tube adapter 200 and related methods are described as being used with an endotracheal tube 150, in some implementations, the endotracheal tube adapter 200 can be used with a laryngeal mask.

While the endotracheal tube adapter 200 is described as having nine longitudinally-extending ribs 216, some adapters can have less than nine ribs (e.g., 0, 1, 2, 3, 4, 5, 6, 7, or 8). Alternatively, or additionally, some adapters can have more than nine ribs (e.g., 10, 11, 12, 13, 14, etc.). The size and number of longitudinally-extending ribs 216 can be determined to provide a gripping surface for the practitioner 400 while satisfying manufacturing needs.

While the endotracheal tube adapter 200 is described as having a single lateral inlet 204, some adapters can have more than one lateral inlet placed immediately adjacent to one another. In another example, some adapters can include a plurality of lateral inlets.

A number of systems and methods have been described. Nevertheless, it will be understood that various modifications may be made without departing from the spirit and scope of this disclosure. Accordingly, other embodiments are within the scope of the following claims.

What is claimed is:

1. An endotracheal tube adapter comprises:
a body defining a sidewall that extends along a longitudinal axis from a first longitudinal end of the endotracheal tube adapter to a second longitudinal end of the endotracheal tube adapter;
an outlet at the first longitudinal end of the body;
a first inlet at the second longitudinal end of the body, the first inlet configured to attach to a proximal end of an endotracheal tube to fluidically connect a lumen of the endotracheal tube to an interior of the body defined by the sidewall of the body;
a second inlet along the sidewall, the second inlet on a first lateral side of a cylindrical portion of the body between the first longitudinal end of the body and the second longitudinal end of the body, the second inlet being substantially flush with the cylindrical portion of the body; and
a plurality of ribs on a second lateral side of the cylindrical portion of the body opposite of the second inlet, each rib of the plurality of ribs (i) extending parallel to the longitudinal axis and (ii) forming a raised surface extending from the cylindrical portion,
wherein the outlet is configured to attach to a vacuum source for drawing (i) a first portion of air or gas through the first inlet, then through the interior of the body, and then through the outlet toward the vacuum source and (ii) a second portion of air or gas through the second inlet, then through the interior of the body, and then through the outlet toward the vacuum source.

2. The endotracheal tube adapter of claim 1, wherein (i) the outlet is located on a first longitudinal half of the body, and (ii) the first inlet, the second inlet, and the plurality of ribs are located on a second longitudinal half of the body.

3. The endotracheal tube adapter of claim 2, wherein:
a longitudinal length of the body between the first longitudinal end to the second longitudinal end is between 30 mm and 140 mm, and
a maximum diameter of the body is between 16 mm and 34 mm.

4. The endotracheal tube adapter of claim 1, wherein the second inlet has an area that can be blocked to increase an amount of suction provided to the lumen of the endotracheal tube by the vacuum source in proportion to the area in which the second inlet is blocked.

5. The endotracheal tube adapter of claim 4, wherein when the vacuum source is attached to the outlet, the endotracheal tube is attached to the first inlet, the vacuum source generates suction, and the area in which the second inlet is blocked is substantially equal to an entire area of the second inlet, the lumen of the endotracheal tube is subjected to substantially all suction provided by the vacuum source.

6. The endotracheal tube adapter of claim 5, wherein when the vacuum source is attached to the outlet, the endotracheal tube is attached to the first inlet, the vacuum source generates suction, and the second inlet is open, the first inlet and the lumen of the endotracheal tube is subjected to substantially no suction provided by the vacuum source.

7. The endotracheal tube adapter of claim 4, wherein the plurality of ribs define a gripping surface for a first digit of a hand of a practitioner while a second digit of the hand of the practitioner can be used to block the second inlet to increase the amount of suction provided to the endotracheal tube.

8. The endotracheal tube adapter of claim 1, wherein (i) the second inlet comprises a circular or an elliptical hole that extends through the sidewall of the body on the first lateral side of the body without extending through the sidewall of the body on the second lateral side of the body, and (ii) a longitudinal length of the plurality of ribs is greater than a diameter or a dimension of the second inlet.

9. The endotracheal tube adapter of claim 8, wherein the second inlet comprises the elliptical hole, the elliptical hole has a major axis aligned in a direction of the longitudinal axis and a minor axis aligned in a circumferential direction defined by the longitudinal axis, and the longitudinal length of the plurality of ribs is greater than (i) a first dimension of the elliptical hole along the major axis and (ii) a second dimension of the elliptical hole along the minor axis.

10. The endotracheal tube adapter of claim 1, wherein the longitudinal axis defines a circumferential direction, and the plurality of ribs comprise three or more ribs defining a uniform spacing the circumferential direction between each pair of adjacent ribs of the three or more ribs.

11. The endotracheal tube adapter of claim 10, wherein a first side of each respective rib of the three or more ribs extends in a same direction, the same direction being transverse to the longitudinal axis.

12. The endotracheal tube adapter of claim 10, wherein (i) the three or more ribs comprise a first rib positioned along a first radial axis extending from the longitudinal axis and a second rib positioned along a second radial axis extending from the longitudinal axis, and (ii) each rib of the three or more ribs is positioned between the first radial axis and the second radial axis.

13. The endotracheal tube adapter of claim 12, wherein the three or more ribs comprise nine ribs disposed within a 137 degree angle along the circumferential direction on the body.

14. The endotracheal tube adapter of claim 1, wherein:
the body is asymmetric about a first plane that is perpendicular to the longitudinal axis and intersects each rib of the plurality of ribs and the second inlet,
the body is symmetric about a second plane that extends longitudinally along the body, passes through the longitudinal axis and the second inlet, and is perpendicular to the first plane,
the body is asymmetric about a third plane that is perpendicular to the first and second planes, and
the third plane intersects the body without intersecting the plurality of ribs or the second inlet.

15. The endotracheal tube adapter of claim 1, wherein:
the body is an integrally formed body comprising first, second, third, and fourth longitudinal sections,
the first longitudinal section (i) extends from the first longitudinal end of the body to the second longitudinal section, and (ii) defines a barbed connection at the outlet of the body,
the second longitudinal section extends from the first longitudinal section to the third longitudinal section,
the third longitudinal section (i) extends from the second longitudinal section to the fourth longitudinal section, and (ii) defines the second inlet and the plurality of ribs,
the fourth longitudinal section (i) extends from the third longitudinal section to the second longitudinal end of the body, and (ii) defines the first inlet, and
the second longitudinal section has a minimum transverse dimension that less than (i) a maximum transverse dimension of the first longitudinal section, (ii) a maximum transverse dimension of the third longitudinal section, and (iii) a maximum transverse dimension of the fourth longitudinal section.

16. The endotracheal tube adapter of claim 15, wherein a first longitudinal length of the first longitudinal section is greater than (i) a second longitudinal length of the second longitudinal section, (ii) a third longitudinal length of the third longitudinal section, and (iii) a fourth longitudinal length of the fourth longitudinal section.

17. The endotracheal tube adapter of claim 15, wherein the second longitudinal section comprises:
a first tapered portion having the minimum transverse dimension and extending along a first angle with respect to the longitudinal axis; and
a second tapered portion that tapers radially outward from the first tapered portion to the third longitudinal section along a second angle with respect to the longitudinal axis, the second angle being greater than the first angle.

18. The endotracheal tube adapter of claim 17, wherein a first longitudinal length of the first tapered portion is substantially equal to a second longitudinal length of the second tapered portion.

19. The endotracheal tube adapter of claim 15, wherein the plurality of ribs are recessed relative to a longitudinal end of the second longitudinal section in which the third longitudinal section is adjacent to, and a longitudinal end of the fourth longitudinal section in which the third longitudinal section is adjacent to.

20. The endotracheal tube adapter of claim 15, wherein:
a first inner surface of the first longitudinal section is tapered relative to the longitudinal axis such that an inner diameter of the first longitudinal section increases from a minimum at the first longitudinal end of the body to a maximum at a longitudinal end of the first longitudinal section,
a second inner surface of the second longitudinal section extends longitudinally from the first inner surface of the first longitudinal section and is tapered relative to the longitudinal axis such that an inner diameter of the second longitudinal section increases from a minimum at the longitudinal end of the first longitudinal section to a maximum at a longitudinal end of the second longitudinal section,
a third inner surface of the third longitudinal section extends longitudinally from the second inner surface of the second longitudinal section and is angled relative to the longitudinal axis such that an inner diameter of the third longitudinal section increases from a minimum at the longitudinal end of the second longitudinal end to a maximum at a longitudinal end of the third longitudinal section, and
a fourth inner surface of the fourth longitudinal section extends longitudinally from the third inner surface of the third longitudinal section and is angled relative to the longitudinal axis such that an inner diameter of the fourth longitudinal section increases from a minimum at the longitudinal end of the third longitudinal section to a maximum at the second longitudinal end of the body.

21. The endotracheal tube adapter of claim 1, wherein the body is configured to be held in a hand of a practitioner with a first digit of the hand of the practitioner in contact with the plurality of ribs and a second digit of the hand of the practitioner covering the second inlet while the vacuum source draws the first portion of air or gas through the first inlet.

22. The endotracheal tube adapter of claim 21, wherein the body is configured to be held in the hand of the practitioner with the first digit of the hand of the practitioner in contact with the plurality of ribs and the second digit of the hand of the practitioner at least partially uncovering the second inlet to allow the vacuum source to draw the first portion of air or gas through the first inlet and the second portion of air or gas through the second inlet.

23. The endotracheal tube adapter of claim 22, wherein the body is configured to be held in the hand of the practitioner with the first digit of the hand of the practitioner in contact with the plurality of ribs and the second digit of the hand of the practitioner completely uncovering the second inlet while the vacuum source draws the second portion of air or gas through the second inlet.

24. The endotracheal tube adapter of claim 21, wherein the body is configured to be held in the hand of the practitioner with the first digit of the hand of the practitioner in contact with the plurality of ribs while allowing the practitioner to rotate the body using the first and second digits to selectively cover or uncover the second inlet with the second digit.

* * * * *